United States Patent
Adachi et al.

(10) Patent No.: US 6,298,726 B1
(45) Date of Patent: Oct. 9, 2001

(54) ACOUSTIC IMPEDANCE MEASURING APPARATUS USING ULTRASONIC WAVES

(75) Inventors: Hideo Adachi, Iruma; Shinji Kaneko, Kokubunji, both of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/329,024

(22) Filed: Jun. 9, 1999

(30) Foreign Application Priority Data

Jun. 25, 1998 (JP) .................................................. 10-178861

(51) Int. Cl.[7] .................................................. G01N 29/00
(52) U.S. Cl. .............................................. 73/632; 367/140
(58) Field of Search .............................. 73/632; 310/316; 367/140

(56) References Cited

U.S. PATENT DOCUMENTS

| | | | |
|---|---|---|---|
| 3,972,228 | * 8/1976 | Mansson | 73/67.3 |
| 4,264,837 | * 4/1981 | Gaboriaud | 310/316 |
| 4,277,710 | * 7/1981 | Harwood et al. | 310/316 |

FOREIGN PATENT DOCUMENTS 6-273396 9/1994 (JP) .
2629734 4/1997 (JP) .

* cited by examiner

*Primary Examiner*—Richard A. Moller
(74) *Attorney, Agent, or Firm*—Frishauf, Holtz, Goodman, Langer & Chick, P.C.

(57) ABSTRACT

An acoustic impedance measuring apparatus emits ultrasonic waves to a target measurement object and measures the acoustic impedance of the target measurement object by ultrasonic waves fed back from the target measurement object. This acoustic impedance measuring apparatus includes an ultrasonic transducer, pulse signal generator, signal separator, frequency converter, parameter extractor, and acoustic impedance calculator. The pulse signal generator generates a pulse signal to be applied to the ultrasonic transducer. The signal separator separates, from an output from the ultrasonic transducer, an immediate ultrasonic response signal resulting from ultrasonic waves reflected by the surface of the target measurement object. The frequency converter obtains the frequency characteristics of the immediate ultrasonic response signal. The parameter extractor extracts predetermined parameters from the frequency characteristics. The acoustic impedance calculator calculates the acoustic impedance of the target measurement object by using the parameters extracted by the parameter extractor.

8 Claims, 17 Drawing Sheets

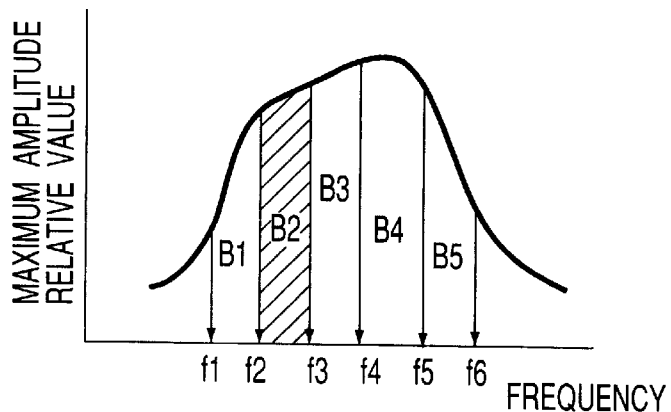
F I G. 12B
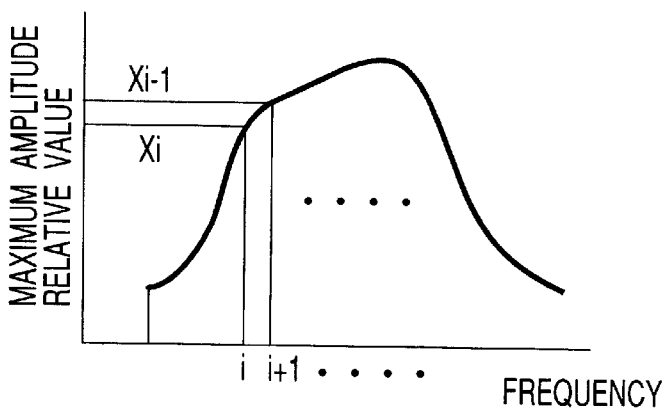
F I G. 12C
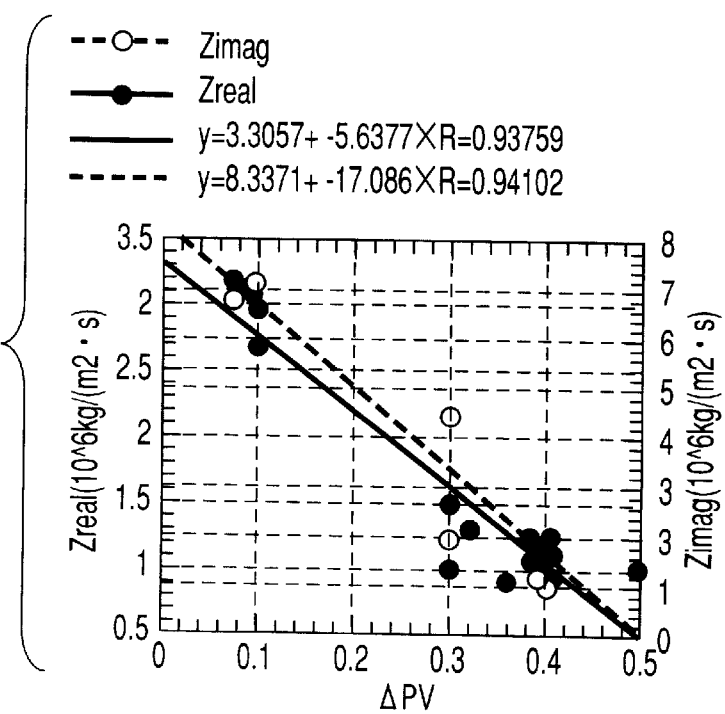
F I G. 13

| | ACOUSTIC IMPEDANCE | | ELASTIC MODULUS | |
|---|---|---|---|---|
| | real | imag | real | imag |
| ΔPV | 0.94 | 0.94 | 0.93 | 0.94 |
| ΔPF | 0.54 | 0.57 | 0.49 | 0.62 |
| ΔCF | 0.52 | 0.42 | 0.52 | 0.43 |
| ΔLo-6 | 0.64 | 0.48 | 0.64 | 0.48 |
| ΔHi-6 | 0.49 | 0.42 | 0.48 | 0.45 |
| ΔBW-6 | 0.44 | 0.39 | 0.46 | 0.39 |
| ΔrBW | 0.14 | 0.21 | 0.18 | 0.25 |
| ΔB1 | 0.73 | 0.76 | 0.75 | 0.77 |
| ΔB2 | 0.94 | 0.91 | 0.94 | 0.89 |
| ΔB3 | 0.31 | 0.31 | 0.28 | 0.22 |
| ΔB4 | 0.47 | 0.47 | 0.52 | 0.46 |
| ΔB5 | 0.41 | 0.40 | 0.45 | 0.43 |
| Δ1stM | 0.71 | 0.80 | 0.73 | 0.78 |
| Δ2ndM | 0.69 | 0.86 | 0.72 | 0.79 |

RELATIONSHIP BETWEEN Zreal, Zimag, AND B2

RELATIONSHIP BETWEEN Zreal, Zimag, AND B2

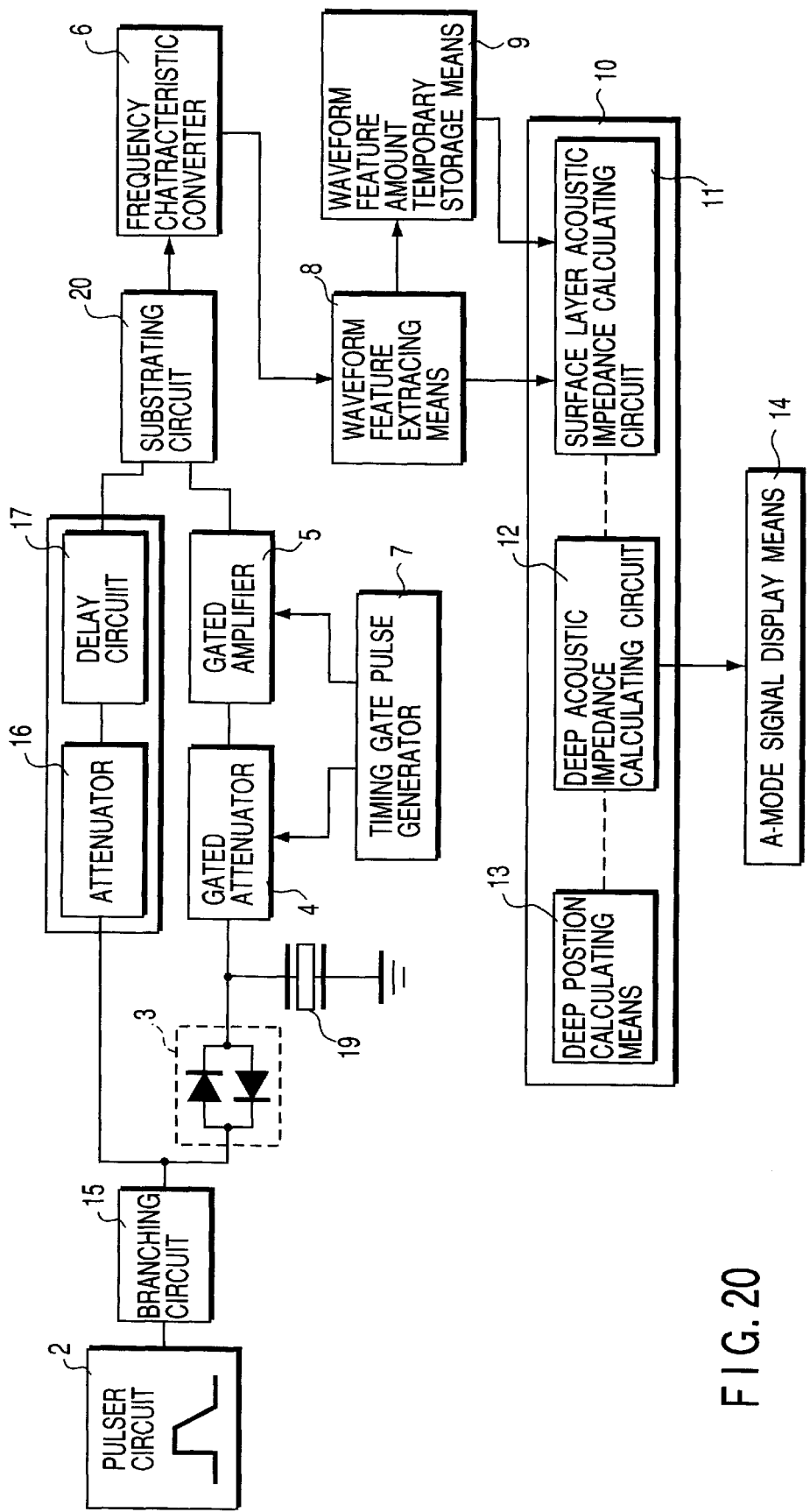
F I G. 20

ACOUSTIC IMPEDANCE MEASURING APPARATUS USING ULTRASONIC WAVES

BACKGROUND OF THE INVENTION

The present invention relates to an acoustic impedance measuring apparatus for measuring the acoustic impedance of a target measurement object by using ultrasonic waves and, more particularly, to an acoustic impedance measuring apparatus for measuring the acoustic impedance from the surface to a deep portion of a target measurement object by using ultrasonic waves.

Conventionally, the research and development of a technology of measuring the physical properties of a vital tissue or of a complicated structure and displaying the measured physical properties in the form of an image have been done.

This technology is particularly important in medical diagnoses.

For example, when this technology is used to discriminate between a benign tumor and a malignant tumor and examine the necessity for a surgical operation, an unnecessary surgical operation can be avoided.

This makes it possible to avoid imposing physical and economical burdens on the patient.

Points presently recognized as problems or subjects of this technology are as follows.

For example, the discrimination between a benign cerebral aneurysm and a malignant cerebral aneurysm requires craniotomy because this discrimination is done by checking the color difference between them.

Also, it is known that many hematomas growing in deep portions of a liver are benign. However, it is in practice difficult to discriminate between a benign hematoma and a hardened cancer tissue, so a surgical operation is necessary for the sake of safety.

This is so because even when a conventional ultrasonic diagnostic apparatus observes a shadow, if the difference between the acoustic impedance of a hematoma and the acoustic impedance of a surrounding normal tissue is small, regardless of whether the former is higher or lower than the latter, similar echo images are displayed.

Also, it is necessary to increase the accuracy of measurement of the depth of a cancer and perform an optimum diagnosis not forcing any excessive burden on a patient.

As an effective solution for these problems and subjects, the development of an image diagnostic apparatus capable of accurately diagnosing the properties of a vital tissue has been desired.

Conventional ultrasonic diagnostic apparatuses use the direction of depth as the time axis of ultrasonic propagation and find the position on this time axis of a tissue whose acoustic impedance has a certain difference from the acoustic impedance of a peripheral tissue.

It is impossible for these apparatuses to find whether the acoustic impedance of an object is higher or lower than the acoustic impedance of a peripheral tissue.

Recently, however, to solve this problem of the conventional ultrasonic diagnostic apparatuses, the research of an ultrasonic diagnostic apparatus which estimates the elastic characteristics as properties of a vital tissue and displays an image of the elastic characteristics is being extensively sought.

For example, Japanese Patent No. 2629734 has disclosed a technology pertaining to an ultrasonic apparatus which measures the elastic characteristics of a target measurement object by applying ultrasonic waves and low-frequency vibrations to the object.

Referring to FIG. 22A, this ultrasonic diagnostic apparatus controls a burst signal (3.5 MHz) generator 204 and a power amplifier 205 to apply ultrasonic waves from an ultrasonic transducer array 202 to a sample 200 as a target measurement object via a gel substance 203.

A display device 212 detects the ultrasonic waves fed back from the sample 200 via the gel substance 203, the ultrasonic transducer array 202, an amplifier 206, a logarithmic amplifier 207, an envelope detector 208, a low-pass filter 209, an A/D converter 210, and a microcomputer 211.

In this measurement, a vibrator 216 which is supported by a spring balancer 213 and driven via a low-frequency oscillator 214 and a power amplifier 215 applies low-frequency vibrations to the sample 200 as a target measurement object via a vibrating plate 201. The vibrations propagate into the sample 200 as a target measurement object.

This propagating vibration pressure applies perturbation to a large number of fine reflectors inside the sample 200 as a target measurement object. The response from the sample 200 as a target measurement object when a reflector receives this perturbation is different from the response when no reflector receives the perturbation.

FIGS. 22B and 22C show the output waveforms of ultrasonic probe waves fed back from the sample 200 as a target measurement object and displayed on the display device 212 when ultrasonic waves are applied to the sample 200 with different low-frequency vibration phases.

FIG. 22D shows a waveform indicating the difference between FIGS. 22B and 22C.

On the basis of a change rate $\Delta E$ shown in FIG. 22D, the susceptivity to perturbation of the interior of the sample 200 as a target measurement object, i.e., the elastic feature of the sample 200 can be known.

In FIG. 22A, reference numeral 217 denotes a timing signal generator for supplying necessary timing signals to the individual units described above.

Also, Jpn. Pat. Appln. KOKAI Publication No. 6-273396 describes an ultrasonic diagnostic apparatus which applies a drive pulse as an input signal as shown in FIG. 23A to an ultrasonic transducer and immediately detects the difference between waveform feature amounts, e.g., maximum amplitudes of an ultrasonic response signal 301 and an echo signal 302, thereby estimating the hardness of a target measurement object.

FIGS. 23C and 23D show FFT (Fast Fourier Transform) images of the ultrasonic response signal 301 and the echo signal 302, respectively, shown in FIG. 23B.

FIG. 24 shows a process flow of this ultrasonic diagnostic apparatus.

In this flow, after blank measurement (step S1), i.e., no-load measurement, a target measurement object is measured (step S2). After that, contact stress measurement (step S3), impulse response characteristic measurement (step S4), transmission signal waveform analysis (step S5), reception signal waveform analysis (step S6), and echo time analysis (step S7) are performed. The waveform feature amounts of the measurement results are compared by comparing the transmission/reception signal waveform analytical values and the blank measurement value (step S8). The comparison result and the echo time are divided into a time response characteristic and a nonlinear elastic value (step S9). Tactile perceptual data is formed from this result and the contact stress (step S10).

This ultrasonic diagnostic apparatus includes an ultrasonic transducer capable of detecting elastic characteristics, i.e., anisotropy in lateral and longitudinal directions, a means for generating a pulse voltage, a means for reading the amplitude and center frequency of a piezoelectric vibration signal excited by this pulse voltage, a means for reading the maximum amplitude and center frequency of an ultrasonic echo signal with respect to an ultrasonic transmission signal which is generated by the piezoelectric vibration signal and propagates in the direction of depth, and a perceptual data processing means for receiving these parameters and converting them into hardness data of a target measurement object.

Unfortunately, the technology disclosed in Japanese Patent No. 2629734 requires a vibrator for applying low-frequency vibrations to a target measurement object and propagating the vibrations inside the object. This vibrator is difficult to miniaturize because a vibrating mechanism is necessary and the vibrating end must be brought into contact with the object. This makes it difficult to apply this technology to an ultrasonic endoscopic system.

Also, in an extracorporeal ultrasonic diagnostic system, low-frequency vibrations are scattered by subcutaneous fat, ribs, and the body cavity. Therefore, it is uneasy to propagate such low-frequency vibrations from the body surface to a target vital tissue.

Additionally, the distribution of stress excited by low-frequency vibrations propagating in the direction of depth of a vital tissue must be uniform along a direction in which an ultrasonic signal propagates.

However, it is extremely difficult to keep constant the stress distribution generated in a vital tissue by propagation.

Furthermore, the presence of fine scattering bodies inside an object is a premise. However, fine scattering bodies are not necessarily present in an actual vital tissue. Also, even when scattering bodies exist, the level of an echo signal from such a scattering body is very low, so the signal may be buried in external noise or apparatus noise.

Accordingly, a special algorithm must be used to extract the echo signal buried in the noise level, and this makes real-time processing difficult.

Since the accuracy of diagnosis of the hardness of an object is insufficient due to the two latter restrictions, the aforementioned discrimination between a benign tumor and a malignant tumor is presumably difficult to perform in the initial stages of tumor growth.

Jpn. Pat. Appln. KOKAI Publication No. 6-273396 describes the technology of inputting the maximum amplitude and center frequency of an ultrasonic response signal (echo signal) as extraction parameters and converting them into hardness data of a target measurement object.

This Jpn. Pat. Appln. KOKAI Publication No. 6-273396, however, does not describe calculations of the characteristics concerning the elasticity of a target measurement object by using a predetermined algorithm.

BRIEF SUMMARY OF THE INVENTION

The present invention has been made in consideration of the above situation, and relates to an acoustic impedance measuring apparatus for measuring the acoustic impedance of a target measurement object by using ultrasonic waves. More particularly, the present invention contributes to realization of an apparatus capable of displaying an image of the characteristic concerning the elasticity of a living body at high resolution and high speed, and has as its object to provide an acoustic impedance measuring apparatus for measuring the acoustic impedance from the surface to a deep portion of a target measurement object by using ultrasonic waves.

To achieve the above object, according to one aspect of the present invention, there is provided a first acoustic impedance measuring apparatus for emitting ultrasonic waves to a target measurement object and measuring the acoustic impedance of the target measurement object from ultrasonic waves fed back from the target measurement object, comprising:

an ultrasonic transducer;

pulse signal generating means for generating a pulse signal to be applied to the ultrasonic transducer;

signal separating means for separating, from an output from the ultrasonic transducer, an immediate ultrasonic response signal resulting from the ultrasonic waves reflected by a surface of the target measurement object;

frequency converting means for obtaining frequency characteristics of the immediate ultrasonic response signal;

parameter extracting means for extracting predetermined parameters from the frequency characteristics obtained by the frequency converting means; and acoustic impedance calculating means for calculating an acoustic impedance of the target measurement object by using the parameters extracted by the parameter extracting means.

A second acoustic impedance measuring apparatus of the present invention further comprises, in addition to the arrangement of the above acoustic impedance measuring apparatus, signal receiving means for receiving an ultrasonic echo signal following the immediate ultrasonic response signal from the output from the ultrasonic transducer and attenuating or amplifying the ultrasonic echo signal. The acoustic impedance calculating means further calculates an acoustic impedance in a deep portion of the target measurement object on the basis of the calculated acoustic impedance of the target measurement object and the ultrasonic echo signal.

A third acoustic impedance measuring apparatus of the present invention is an acoustic impedance measuring apparatus for emitting ultrasonic waves to a target measurement object and measuring an acoustic impedance of the target measurement object from ultrasonic waves fed back from the target measurement object, comprising an ultrasonic transducer, pulse signal generating means for generating a pulse signal to be applied to the ultrasonic transducer, and an acoustic delay medium arranged on a side of an ultrasonic exit surface of the ultrasonic transducer.

A fourth impedance measuring apparatus of the present invention is an acoustic impedance measuring apparatus for emitting ultrasonic waves to a target measurement object and measuring an acoustic impedance of the target measurement object from ultrasonic waves fed back from the target measurement object, comprising an ultrasonic transducer, and pulse signal generating means for generating a pulse signal to be applied to the ultrasonic transducer, the pulse signal having a trapezoidal wave or a first rectangular wave and a succeeding second rectangular wave.

That is, the first acoustic impedance measuring apparatus of the present invention applies a pulse signal to cause the ultrasonic transducer to emit ultrasonic waves to a target measurement object. The apparatus extracts the immediate ultrasonic response signal from an output from the ultrasonic transducer, which is based on the reflected waves. The apparatus obtains the frequency characteristics of this immediate ultrasonic response signal and extracts parameters therefrom. The apparatus measures the acoustic impedance by using the parameters in predetermined relations.

The second acoustic impedance measuring apparatus of the present invention further receives the ultrasonic echo signal following the immediate ultrasonic response signal. The apparatus calculates the acoustic impedance in a deep portion of the target measurement object on the basis of the ultrasonic echo signal and the calculated acoustic impedance of the target measurement object.

The third acoustic impedance measuring apparatus of the present invention includes the acoustic delay medium attached to the ultrasonic exit surface of the ultrasonic transducer.

The fourth acoustic impedance measuring apparatus of the present invention applies a trapezoidal wave or double pulse signals having a first rectangular wave and a succeeding second rectangular wave to the ultrasonic transducer.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 12A to 12C are graphs for explaining waveform feature parameters;

FIG. 13 is a graph showing experimental results for explaining the relationship between a waveform feature parameter (PV) and acoustic impedance;

FIG. 20 is a block diagram showing the arrangement of the second embodiment of the present invention;

DETAILED DESCRIPTION OF THE INVENTION

Figure 1:
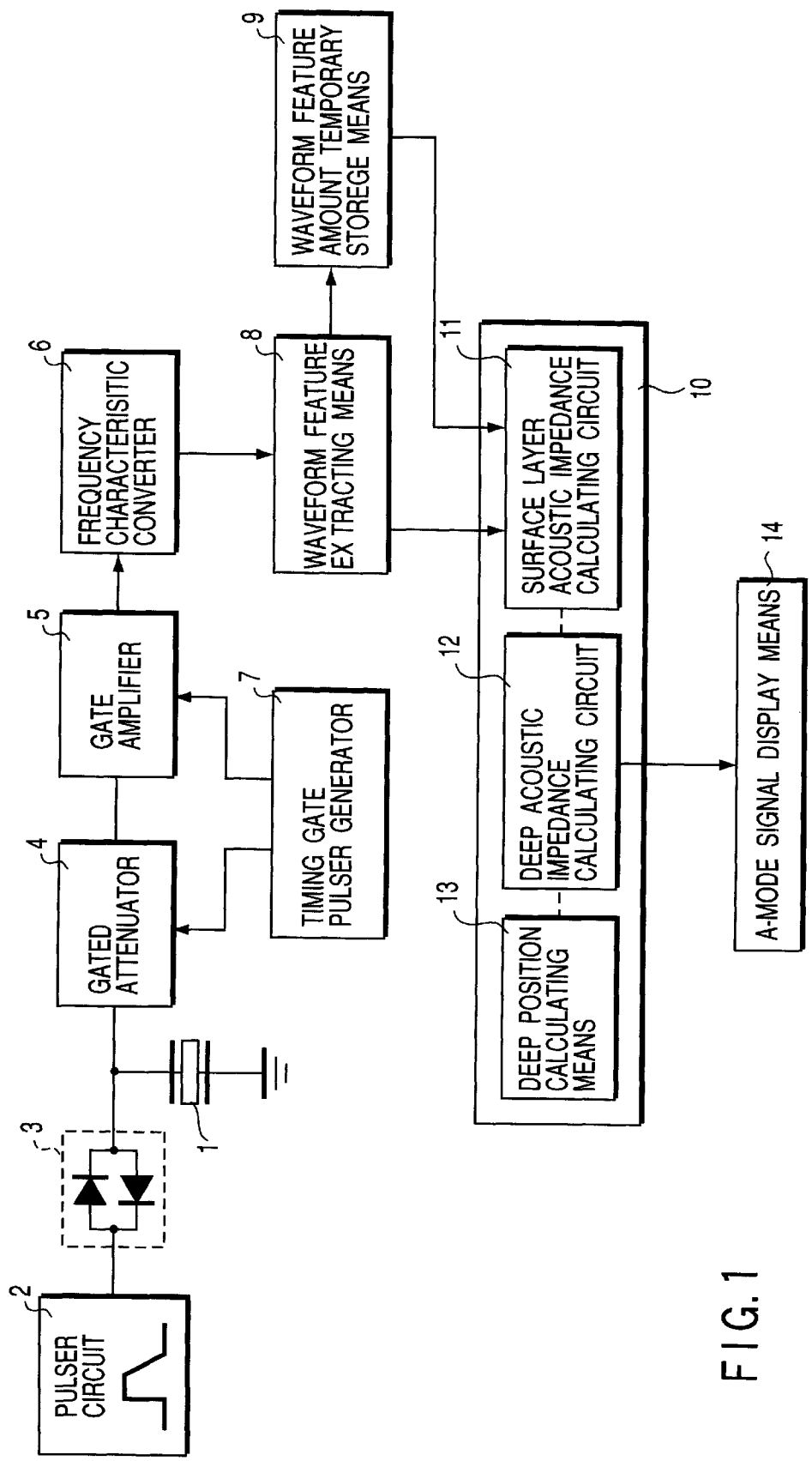
FIG. 1 is a block diagram showing the arrangement of the first embodiment of the present invention.

Reference will now be made in detail to the presently preferred embodiments of the invention and illustrated in the accompanying drawings, in which like reference characters designate like or corresponding parts throughout the several drawings.

Embodiments of the present invention will be described below with reference to the accompanying drawings.

First Embodiment

FIG. 1 is a block diagram showing the arrangement of the first embodiment of an acoustic impedance measuring apparatus according to the present invention.

As shown in FIG. 1, a pulser circuit 2 as a pulse signal generating means is connected to a waveform feature extracting means 8 as a parameter extracting means via a diode circuit 3, a gated attenuator 4, a gated amplifier 5, and a frequency characteristic converter 6 as a frequency converting means.

One terminal of an ultrasonic transducer 1 is grounded, and its other terminal is connected between the diode circuit 3 and the gated attenuator 4.

A timing gate pulse generator 7 is connected to the gated attenuator 4 and the gated amplifier 5.

The timing gate pulse generator 7, the gated attenuator 4, and the gated amplifier 5 are equivalent to a signal separating means and a signal receiving means.

The waveform feature extracting means 8 is connected to a surface layer acoustic impedance calculating circuit 11 via a waveform feature amount temporary storage means 9 and is also directly connected to the surface layer acoustic impedance calculating circuit 11.

This surface layer acoustic impedance calculating circuit 11, a deep acoustic impedance calculating circuit 12, and a deep position calculating circuit 13 are included in an acoustic impedance calculating means 10.

This acoustic impedance calculating means 10 is connected to an A-mode signal display means 14.

To measure the acoustic impedance of a target measurement object, the pulser circuit 2 generates a high-voltage, wideband pulse signal.

This pulse signal is applied to the ultrasonic transducer 1 via the diode circuit 3.

The ultrasonic transducer 1 has a characteristic that a mechanical quality coefficient Qm representing frequency sharpness is relatively larger and, applies ultrasonic waves to the target measurement object in accordance with the pulse signal.

The ultrasonic transducer 1 detects the ultrasonic waves fed back from the target measurement object.

The ultrasonic transducer 1 superposes the detected response signal on the same line as the input pulse signal and outputs the response signal to the gated attenuator 4.

This response signal has an immediate ultrasonic response signal and a succeeding ultrasonic echo signal.

The immediate ultrasonic response signal results from ultrasonic waves reflected by the surface of the target measurement object. When the target measurement object has a layered structure, acoustic impedance information pertaining to the uppermost surface layer can be obtained by this immediate ultrasonic response signal.

The succeeding ultrasonic echo signal results from ultrasonic waves reflected by the internal structure of the target measurement object. Acoustic impedance information concerning a deep portion of the target measurement object can be obtained by this signal.

The timing gate pulse generator 7 controls the gated attenuator 4 and the gated amplifier 5.

While the pulse signal has a finite value on the output line from the ultrasonic transducer 1, the gated attenuator 4 attenuates the signal by a time attenuating function.

The gated amplifier 5 amplifies the pulse signal immediately after the signal voltage becomes 0V.

In this manner, a portion concerning the pulse signal is removed from the output from the ultrasonic transducer 1 to separate the immediate ultrasonic response signal and the ultrasonic echo signal.

By the function of an acoustic delay medium (to be described later) arranged on the ultrasonic exit surface of the ultrasonic transducer, the pulse signal and the response signal come to positions where they do not overlap each other along the time axis on the output line of the ultrasonic transducer 1.

The output from the gated amplifier 5 is input to the frequency characteristic converter 6 where a time signal is converted into a frequency characteristic signal for each of the immediate response signal and the ultrasonic echo signal.

The waveform feature extracting means 8 receives this frequency characteristic signal and extracts waveform feature parameters from the signal.

These waveform feature parameters are input to the surface layer acoustic impedance calculating circuit 11.

The surface layer impedance calculating circuit 11 also receives no-load waveform feature parameters temporarily prestored in the waveform feature amount temporary storage means 9, i.e., waveform feature parameters measured when no target measurement object is brought into contact with the ultrasonic transducer 1.

The surface layer acoustic impedance calculating circuit 11 applies waveform feature parameters pertaining to the immediate ultrasonic response signal, among other extracted waveform feature parameters, and the no-load waveform feature parameters to a predetermined calibration expression, thereby calculating the acoustic impedance in the surface layer of the target measurement object.

On the basis of waveform feature parameters of the ultrasonic echo signal and the surface layer acoustic impedance calculated by the surface layer acoustic impedance calculating circuit 11, the deep acoustic impedance calculating circuit 12 sequentially calculates the acoustic impedances in deep portions by using a predetermined expression.

The deep position calculating means 13 calculates a deep position on the basis of each ultrasonic echo signal.

The A-mode signal display means 14 displays the calculation results in the A mode, i.e., graphically displays the relationship between the position in the direction of depth and the acoustic impedance along one ultrasonic beam having no information in the direction of plane.

The characteristic portions of the present invention will be described in detail next.

First, the output waveform from the pulser circuit 2 will be described.

The ultrasonic transducer 1 generates ultrasonic waves in accordance with the pulse signal generated by the pulser circuit 2.

When the pulse wave is input to the ultrasonic transducer 1, the output ultrasonic waves usually do not immediately stop, and the vibrations continue for some time while attenuating. That is, a tail of the vibrations exists.

When ultrasonic waves are used in measurement, on the other hand, the depth of an object is estimated by the feedback time of the ultrasonic waves. Therefore, the time during which ultrasonic waves are generated is desirably as short as possible.

The present invention solves the problem of this tail by using a combination of a trapezoidal wave or double rectangular pulses having a first rectangular wave and a succeeding second rectangular wave, as the pulse signal generated by the pulser circuit 2.

The trapezoidal pulse signal will be described below with reference to FIGS. 2A to 2C.

The ultrasonic transducer 1 as a piezoelectric element used in this first embodiment is a differentiating element which excites piezoelectric vibrations at the moment the applied voltage changes.

Figure 2A:
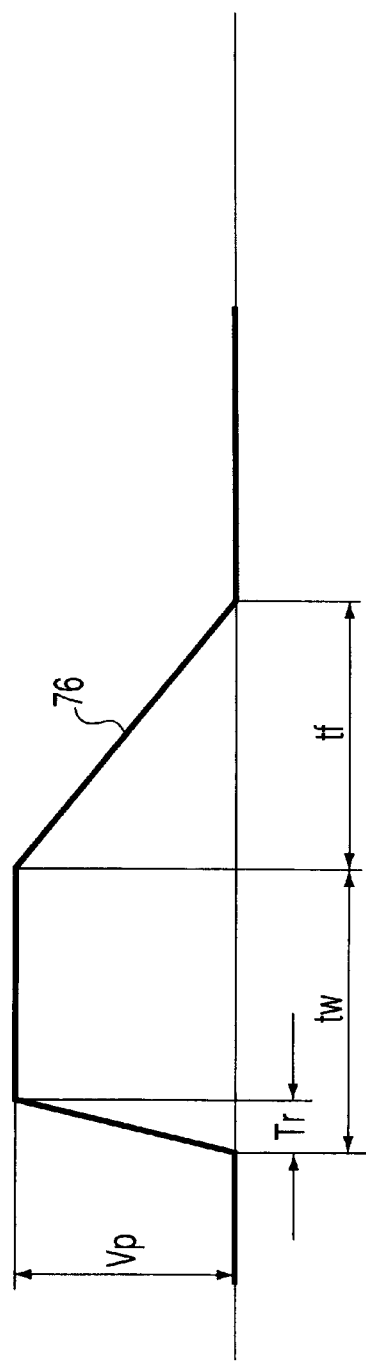
FIGS. 2A to 2C are timing charts for explaining a trapezoidal drive pulse signal.
Figure 2B:
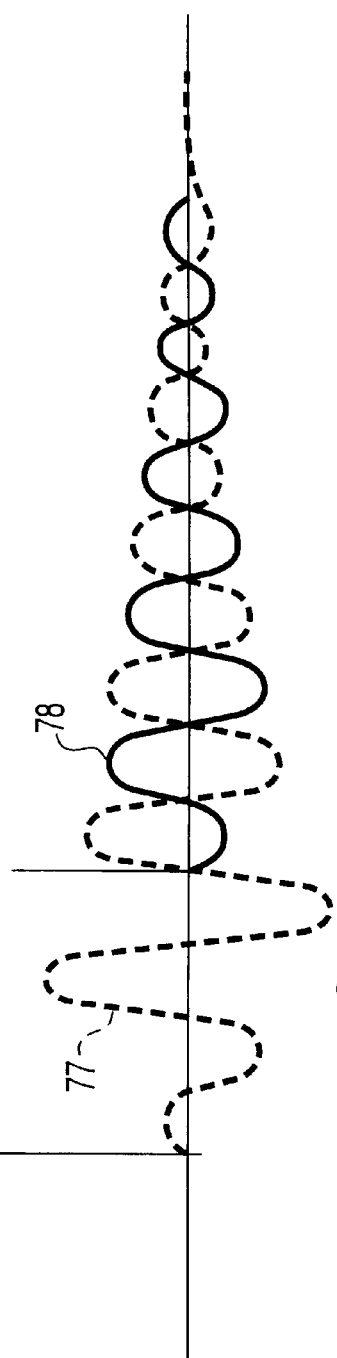

Referring to FIGS. 2A and 2B, let tr and tf be the rise time and the fall time, respectively, of a trapezoidal pulse 76, tw be the pulse width which is the time between the rise start time and the fall start time of the trapezoidal pulse 76, and T be the reciprocal of a center frequency f0 of the ultrasonic transducer 1.

If tr is shorter than ½ of T when this trapezoidal pulse 76 is input to the ultrasonic transducer 1, a piezoelectric vibration 77 having a relatively large amplitude proportional to an applied voltage Vp is excited.

If tf is longer than ½ of T, a piezoelectric vibration 78 proportional to the slope of the interval tf of the trapezoidal pulse 76 and having a phase opposite to that of the piezoelectric vibration 77 is excited.

Figure 2C:
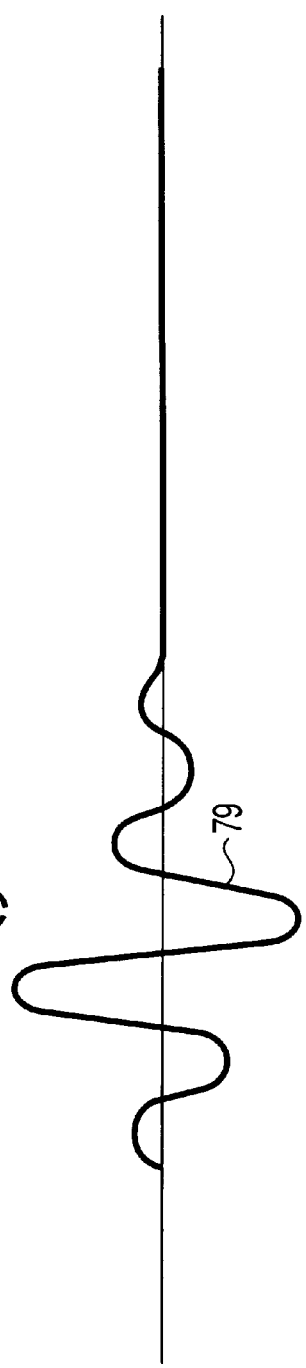

When these piezoelectric vibrations 77 and 78 are superposed by setting tw to be an integral multiple of T, a synthetic wave 79 as shown in FIG. 2C is obtained.

In this synthetic wave 79, the piezoelectric vibrations 77 and 78 are superposed, and the tail of the piezoelectric vibration 77 and the piezoelectric vibration 78 cancel each other. So, the vibration converges within a short time.

In this first embodiment, the pulser circuit 2 includes a waveform adjusting means and can independently adjust the pulse width tw, the fall time tf, and the maximum voltage Vp of the trapezoidal pulse signal.

Figure 3A:
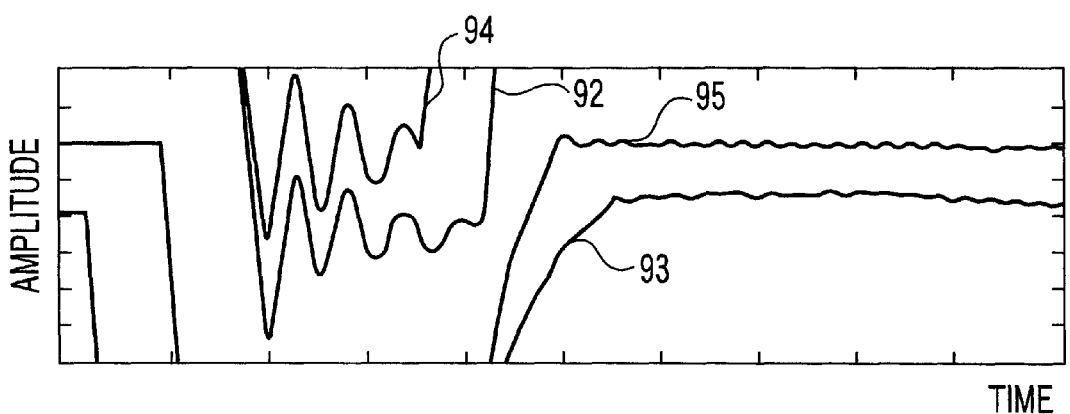
FIGS. 3A to 3C are graphs showing experimental results for explaining the effect of the trapezoidal drive pulse signal.
Figure 3B:
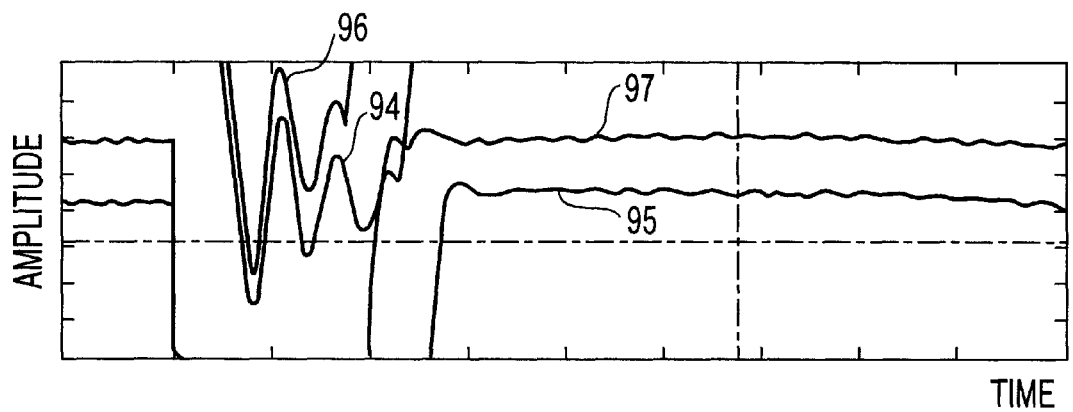
Figure 3C:
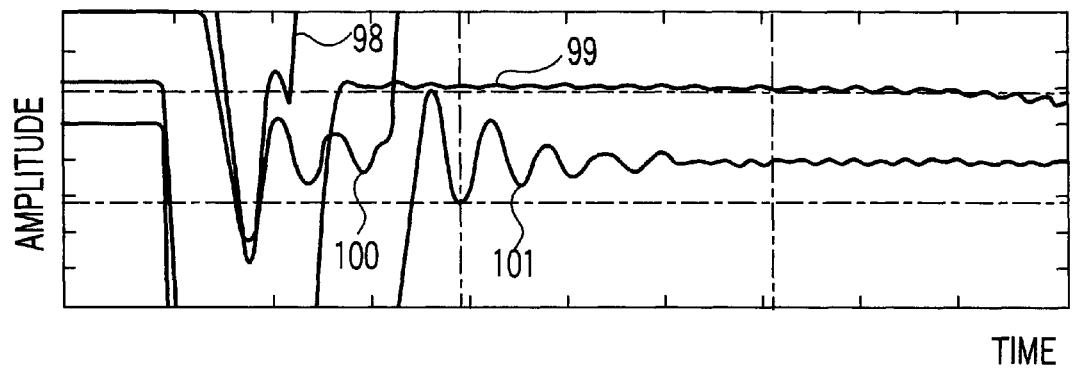

FIGS. 3A to 3C show the results of experimental confirmation of the adjustment.

In this experiment, the waveforms of synthetic piezoelectric vibration signals were measured while the applied voltage Vp and the rise time tr of the trapezoidal pulse were fixed and the pulse width tw and the fall time tf were independently changed.

As the transducer 1, a transducer having a center frequency of 7.5 MHz and including no back packing material was used.

FIGS. 3A to 3C show both of a drive signal for driving the ultrasonic transducer and a piezoelectric vibration signal as the corresponding response.

In each of FIGS. 3A to 3C, the drive signal is shown on the left side, and the synthetic piezoelectric vibration signal is shown in a portion from the left of the center to the right side.

A tail is shown in detail in the piezoelectric response signal. A portion having a large amplitude extends outside the range of each graph.

The combination of curves 100 and 101 indicates one synthetic piezoelectric vibration signal.

The conditions were tw=(n+½)T, n=2, and tf=90 ns (=0.75 T).

A large piezoelectric vibration corresponding to a maximum voltage holding portion of the trapezoid is observed. However, no damping corresponding to the trailing edge of the drive wave occurs, and the large piezoelectric vibration remains.

Each of the combinations of curves 92 and 93, 94 and 95, 96 and 97, and 98 and 99 indicates a synthetic piezoelectric vibration signal.

The conditions were tw=(n+¼)T, n=4, 3, 2, 1, and tf=2.3 T, 2.3 T, 0.88 T, and 0.95 T, respectively.

A large piezoelectric vibration corresponding to a maximum voltage holding portion of the trapezoid is observed. Also, damping corresponding to the trailing edge of the drive wave well has occurred.

Accordingly, the piezoelectric vibration signal rapidly attenuates.

As described above, it was experimentally confirmed that the piezoelectric response signal of the ultrasonic transducer 1 can be rapidly attenuated by using a trapezoidal pulse.

When a trapezoidal wave is used as the pulse signal and its rise time is fixed to, e.g., ½ of T or less, a large-amplitude piezoelectric vibration which is not damped by this change of the leading edge is excited.

This piezoelectric vibration attenuates in proportion to the reciprocal of the mechanical quality coefficient Qm of the transducer in the plateau of the trapezoidal wave. However, another piezoelectric vibration is excited at the trailing edge of the trapezoidal wave.

If the time of this trailing edge is larger than ½ of T, the phase of the latter piezoelectric vibration is opposite to that of the former piezoelectric vibration, and the amplitude of the latter is smaller. The degree of this amplitude is determined in accordance with the peak value of the trapezoidal wave.

When the width of the trapezoidal wave is optimally adjusted, the piezoelectric response signal excited at the trailing edge of the trapezoidal wave overlaps, in opposite phases, the tail of the piezoelectric vibration excited at the leading edge of the trapezoidal wave. Consequently, these vibrations cancel each other to form essentially no vibration waveform in the overlapping region.

As described above, a piezoelectric vibration is obtained in which a large-amplitude vibration excited at the leading edge of the trapezoid continues to the fall time of the trapezoid and almost no vibration occurs after that.

In the present invention, this operation is called dynamic damping (DD) for the sake of convenience.

Experimentally found particularly preferable conditions are that the pulse width tw of the trapezoidal pulse signal satisfies tw=(n+¼)T where n is an integer from 1 to 5 and the fall time tf of the trapezoidal pulse signal satisfies tf=(r+¼)T where r is a real number from 0.5 to 10.

In the present invention as described above, an ultrasonic pulse having a large vibration amplitude and a small pulse width can be obtained by dynamic damping (DD).

This allows the present invention to perform acoustic impedance detection having high resolution in the direction of depth of a target measurement object and high detection sensitivity for the difference between acoustic impedances of the object.

A case where the pulse signal has rectangular waves will be described below with reference to FIGS. 4A to 4C and 5A to 5C.

If this is the case, the pulser circuit 2 generates a pulse signal having a first rectangular wave and a succeeding second rectangular wave.

A case where the first and second rectangular waves have the same polarity will be described first.

Figure 4A:
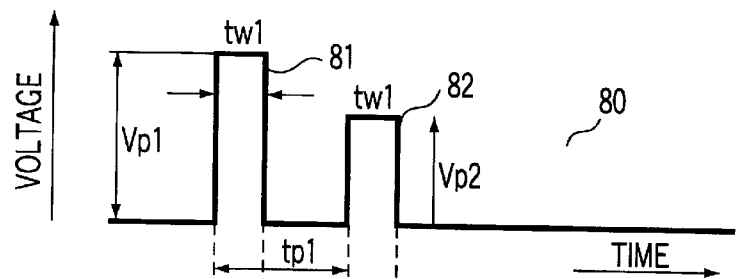
FIGS. 4A to 4C are timing charts for explaining a rectangular drive pulse signal.

More specifically, as shown in FIG. 4A, a drive pulse signal 80 generated by the pulser circuit 2 has a first rectangular pulse 81 having a pulse width of ½ T and a peak value Vp1 and a second rectangular pulse 82 which follows the first rectangular pulse 81 after a time tp and has a pulse width of ½ T and a peak value Vp2.

Vp1 is higher than and has the same polarity as Vp2.

Figure 4B:
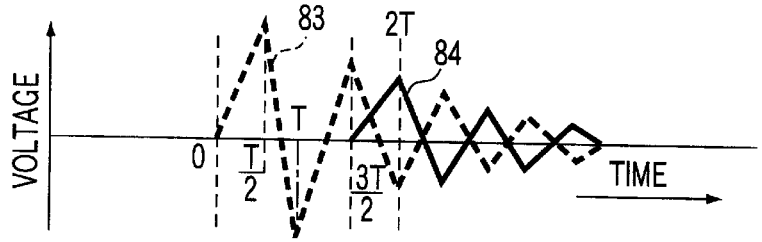

As shown in FIG. 4B, the ultrasonic transducer 1 to which the above pulse signal generated by the pulser circuit 2 is applied generates a piezoelectric vibration 83 corresponding to the first rectangular pulse 81 and a piezoelectric vibration 84 corresponding to the second rectangular pulse 82.

Since the peak value Vp2 of the second rectangular pulse 82 is smaller than the peak value Vp1 of the first rectangular pulse 81, the amplitude of the piezoelectric vibration 84 is smaller than the amplitude of the piezoelectric vibration 83.

If the interval tp between the first and second rectangular pulses 81 and 82 is set such that the phase difference is 3 T/2, the two piezoelectric vibrations overlap and cancel each other after that.

Figure 4C:
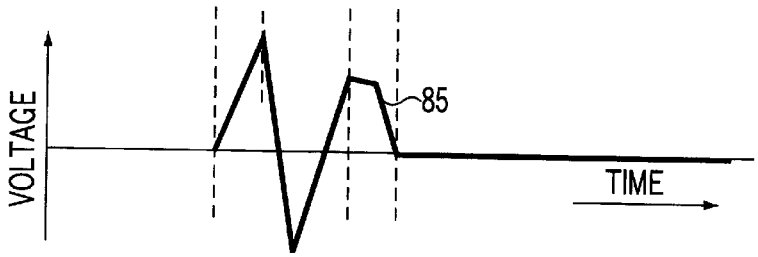

Consequently, as shown in FIG. 4C, a piezoelectric vibration 85 has zero amplitude after a predetermined time.

If this is the case, the phase difference in the interval tp between the first and second rectangular pulses 81 and 82 is not necessarily restricted to 3 T/2 and can be an odd-number multiple of T/2.

This is also confirmed by performing Laplace transform for the drive pulse waveform, multiplying the outcome by the propagation constant (frequency characteristic) of the ultrasonic transducer 1, and performing inverse Laplace transform for the product, because the above piezoelectric vibration 85 is obtained by this operation.

A case where the first and second rectangular waves have opposite polarities will be described below.

Figure 5A:
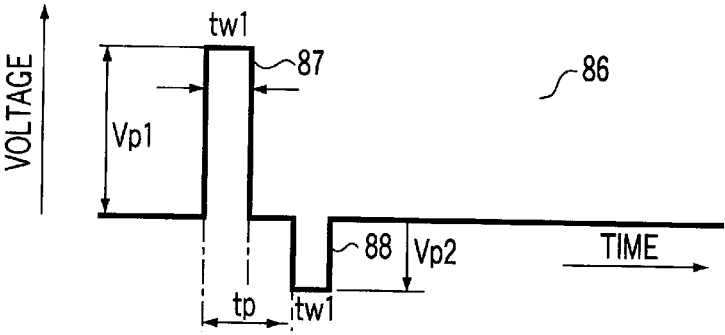
FIGS. 5A to 5C are timing charts for explaining a rectangular drive pulse signal.

More specifically, as shown in FIG. 5A, a drive pulse signal 86 generated by the pulser circuit 2 has a first rectangular pulse 87 having a pulse width of ½ T and a peak value Vp1 and a second rectangular pulse 88 which follows the first rectangular pulse 87 after a time tp and has a pulse width of ½ T and a peak value Vp2.

The absolute value of Vp1 is larger than that of Vp2, and Vp1 and Vps have opposite polarities.

Figure 5B:
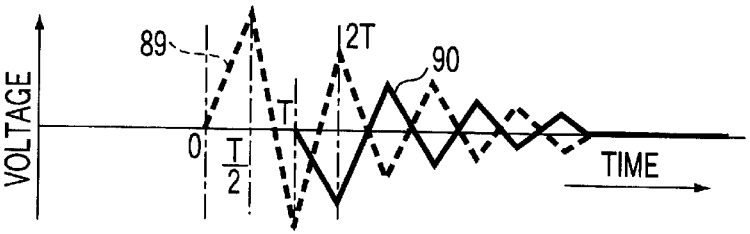

As shown in FIG. 5B, the ultrasonic transducer 1 to which the above pulse signal 86 generated by the pulser circuit 2 is applied generates a piezoelectric vibration 89 corresponding to the first rectangular pulse 87 and a piezoelectric vibration 90 corresponding to the second rectangular pulse 88.

Since the absolute value of the peak value Vp2 of the second rectangular pulse 88 is smaller than the absolute value of the peak value Vp1 of the first rectangular pulse 87, the amplitude of the piezoelectric vibration 90 is smaller than the amplitude of the piezoelectric vibration 89.

If the interval tp between the first and second rectangular pulses 87 and 88 is set such that the phase difference is T (or an integral multiple of T), the two piezoelectric vibrations overlap and cancel each other after that.

Figure 5C:
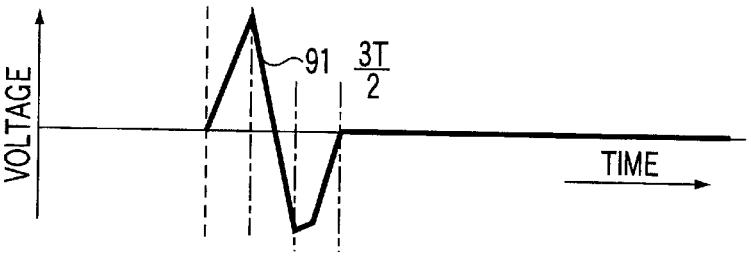

Consequently, as shown in FIG. 5C, a piezoelectric vibration 91 has zero amplitude after a predetermined time.

As described above, the pulse signal has rectangular waves, and the first and second pulse signals can have the same polarity or different polarities. However, the pulser circuit 2 has an internal waveform adjusting means and can independently adjust the position of the first pulse signal on the time axis, the position of the second pulse signal on the time axis, the maximum voltage of the first pulse signal, and the maximum voltage of the second pulse signal.

In the present invention as described above, a pulse signal having a first rectangular wave and a succeeding second rectangular wave is applied to the ultrasonic transducer. Consequently, it is possible to allow vibrations generated in accordance with the first and second rectangular waves by the ultrasonic transducer to cancel each other and thereby attenuate the vibrations of the ultrasonic transducer within a short time.

For example, when a first rectangular wave whose pulse width is ½ of the reciprocal of the center frequency T of the ultrasonic transducer 1 is applied to the ultrasonic transducer 1, a piezoelectric vibration is excited in the ultrasonic transducer 1 and makes an attenuating motion having a period of T seconds.

Following this first rectangular wave, a second rectangular wave whose pulse width is ½ T and absolute value of the amplitude is smaller than that of the first rectangular wave is applied to the ultrasonic transducer 1. Consequently, a piezoelectric vibration is similarly excited in the ultrasonic transducer 1 and makes an attenuating motion having the period T.

By adjusting the phases and amplitudes of the two rectangular waves by using the internal waveform adjusting means of the purser circuit 2, the piezoelectric vibration corresponding to the second rectangular wave can be superposed, with an appropriate amplitude and an opposite phase, on the tail of the piezoelectric vibration corresponding to the first rectangular wave. Therefore, no piezoelectric vibrations are observed after the trailing edge of the second rectangular wave.

If the second rectangular wave has the same polarity as the first rectangular wave, the internal waveform adjusting means of the pulser circuit 2 is used to adjust the difference between the rise times of the first and second rectangular waves to an odd-number multiple of T/2. Consequently, the same good result as above is obtained.

If the second rectangular wave has the opposite polarity to that of the first rectangular wave, the internal waveform adjusting means of the pulser circuit 2 is used to adjust the difference between the rise times of the first and second rectangular waves to an integral multiple of T. Consequently, the same good result as above is obtained.

In the present invention as described above, the technique of dynamic damping (DD) is applied to rectangular waves as well as to trapezoidal waves, so an ultrasonic pulse having a small pulse width can be obtained.

Accordingly, the present invention can perform acoustic impedance detection having high resolution in the direction of depth of a target measurement object and high detection sensitivity for the difference between acoustic impedances of the object.

Note that when dynamic damping (DD) is performed by using a trapezoidal wave, it is necessary to control the slopes of the leading and trailing edges, so a high-speed, high-output linear amplifier is required.

In contrast, when a rectangular wave is used, a desired waveform can be formed by a simple ON/OFF operation by switching output devices. This can make a high-speed, high-output circuit inexpensive and is also advantageous in miniaturization.

Next, the structure of the ultrasonic transducer as one characteristic feature of the present invention, particularly, the acoustic delay medium arranged on the ultrasonic exit surface will be described below.

When the ultrasonic exit surface of the ultrasonic transducer is brought into direct contact with a target measurement object, a waveform in which the pulse signal applied from the pulser circuit to the ultrasonic transducer and the immediate ultrasonic response signal resulting from the ultrasonic waves reflected by the surface of the target measurement object are superposed is generally observed in the output from the ultrasonic transducer.

The immediate ultrasonic response signal contains information concerning the elasticity near the surface of the target measurement object. This immediate ultrasonic response signal must be separated from the pulse signal.

The immediate ultrasonic response signal can be separated from the pulse signal by using an electric circuit.

When an electric circuit is used, however, it is extremely difficult to stably separate the immediate ultrasonic response signal having a high-frequency component as a signal having low noise and small base line variations.

In this first embodiment, therefore, the acoustic delay medium is arranged on the ultrasonic exit surface of the ultrasonic transducer to delay the time the immediate ultrasonic response signal reaches the ultrasonic transducer.

Since this deviates the positions of the pulse signal and the immediate ultrasonic response signal along the time axis, the two signals can be easily separated.

The ultrasonic transducer and the acoustic delay medium in this first embodiment will be described below with reference to FIGS. 6 to 10.

Figure 6:
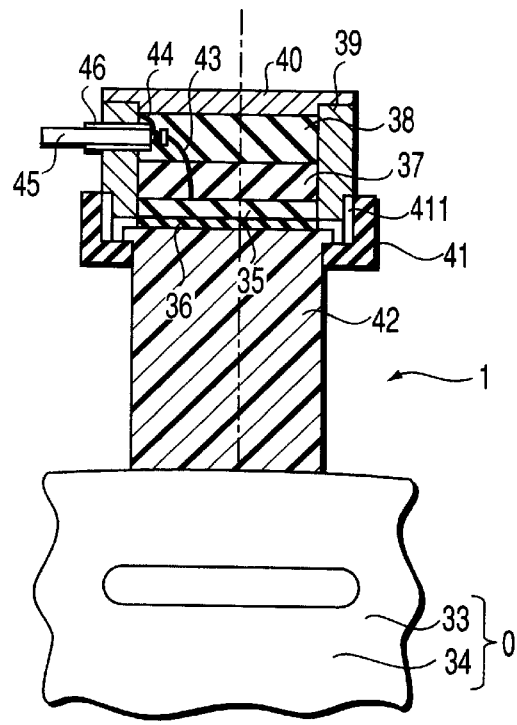
FIG. 6 is a view showing the arrangement of an ultrasonic transducer additionally having an acoustic delay medium.

FIG. 6 shows the state in which the ultrasonic transducer 1 is contacting a human body as the target measurement object O via an acoustic delay medium 42.

In FIG. 6, reference numerals 33 and 34 denote normal and abnormal tissues, respectively, of the target measurement object O.

Reference numeral 35 denotes a piezoelectric element of the ultrasonic transducer 1; 36, an acoustic matching layer; 37, a load member; 38, a sealing member; 39 and 40, a housing; 41, a press tool; 411, the thread of the press tool 41; 42, an acoustic delay medium; and 43 to 46, wires.

The piezoelectric element 35 is made of, e.g., PZT ceramic polarized in the direction of thickness. Since the center frequency f0 described earlier relates to a thickness, the thickness of this piezoelectric element 35 is determined in accordance with the target measurement frequency.

The mechanical quality coefficient Qm indicating the frequency sharpness of the piezoelectric element 35 is desirably 50 or less.

The layered load member 37 as the back surface member of the piezoelectric element 35 desirably has a low acoustic impedance, and preferably an acoustic impedance of $1 \times 10^5$ to $15 \times 10^6$ $kgm^{-2}$ $sec^{-1}$.

If the acoustic impedance of the load member 37 is $1 \times 10^5$ $kgm^{-2}$ $sec^{-1}$ or less, the mechanical quality coefficient Qm of the ultrasonic transducer goes to far rise to make the damping effect during reception unsatisfactory.

Also, if the acoustic impedance of the load member 37 is $1 \times 10^5$ $kgm^{-2}$ $sec^{-1}$ or less, unnecessary vibrations occur to make effective dynamic damping (DD) impossible to perform.

More specifically, although the load member 37 can be an air load, the load member 37 is desirably a fixed load member to maintain the mechanical strength. For example, cork or silicone gel having a specific gravity of 0.7 or less is suitable.

An example of the gel is β Gel (manufactured by Co. Ltd. Siegel).

If the acoustic impedance of the load member 37 is $15 \times 10^6$ $kgm^{-2}$ $sec^{-1}$ or less, this acoustic impedance is lower than that of the piezoelectric element 35. Therefore, a piezoelectric vibration excited by the pulse signal propagates to the load member 37 with no loss, so a large vibration amplitude can be obtained.

This allows the ultrasonic transducer 1 to apply a large ultrasonic vibration to the target measurement object O.

Since, however, the damping effect during reception becomes unsatisfactory, the acoustic impedance of the load member 37 must be $1 \times 10^5$ $kgm^{-2}$ $sec^{-1}$ or more.

This acoustic impedance is realized by connecting the acoustic delay medium 42, and this allows detection of deep information of the target measurement object at high sensitivity.

On the other hand, if the acoustic impedance of the load member 37 is $15 \times 10^6$ $kgm^{-2}$ $sec^{-1}$ or more, the detection sensitivity of the ultrasonic transducer 1 lowers. Consequently, no high-quality acoustic impedance images can be obtained.

Optimum values of an acoustic impedance Zmat and a thickness tmat of the acoustic matching layer 36 can be calculated by $$Zmat = (Zprop \cdot Zpiezo)^{1/2}$$

$$tmat = Vmat/4fc$$

where Zprop is the acoustic impedance of the acoustic delay medium 42, Zpiezo is the acoustic impedance of the piezoelectric element 35, and Vmat is the sonic velocity of the material of the acoustic matching layer 36.

If, however, the target measurement object is a living body, a material meeting the above Zmat equation and readily processable is hard to obtain.

Hence, the general approach is, in many instances, to use polystyrene which produces little ultrasonic propagation loss, has an acoustic impedance not equal to but relatively close to that of a living body, and is readily processable, as the acoustic delay medium 42, and use an epoxy resin as the acoustic matching layer 36.

Figure 7:
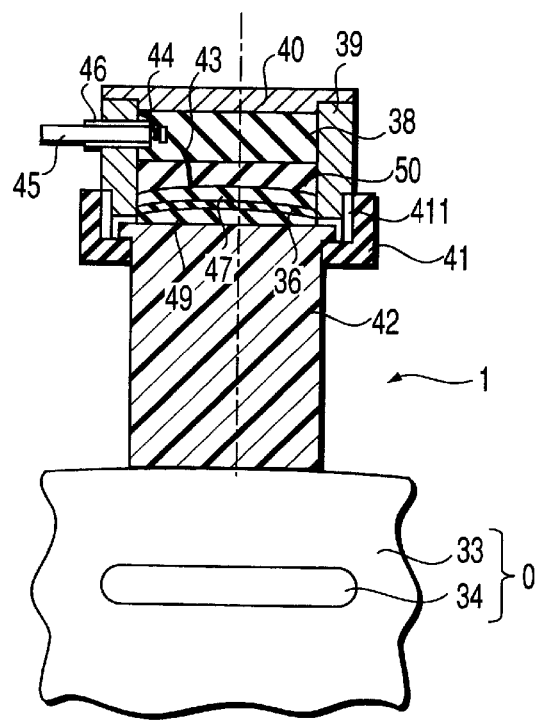
FIG. 7 is a view showing the arrangement of an ultrasonic transducer additionally having an acoustic delay medium.

FIG. 7 shows the first modification of the structure shown in FIG. 6.

Although a detailed description of the same parts as shown in FIG. 6 will be omitted, a piezoelectric element 47 has a concave surface and generates convergent ultrasonic waves.

If the same acoustic delay medium 42 as shown in FIG. 6 is used, a gap 49 is formed. Therefore, an acoustic coupler material, such as echo gel, which has flowability and does not easily cause ultrasonic attenuation is so arranged as not to form air bubbles or air layers.

The shape of a load member 50 is changed in accordance with the concave surface of the piezoelectric element 47.

The rest of the structure is exactly the same as in FIG. 6.

With the structure shown in FIG. 7, it is possible to use convergent ultrasonic waves and improve the resolution in the direction of plane of the ultrasonic transducer 1.

Figure 8:
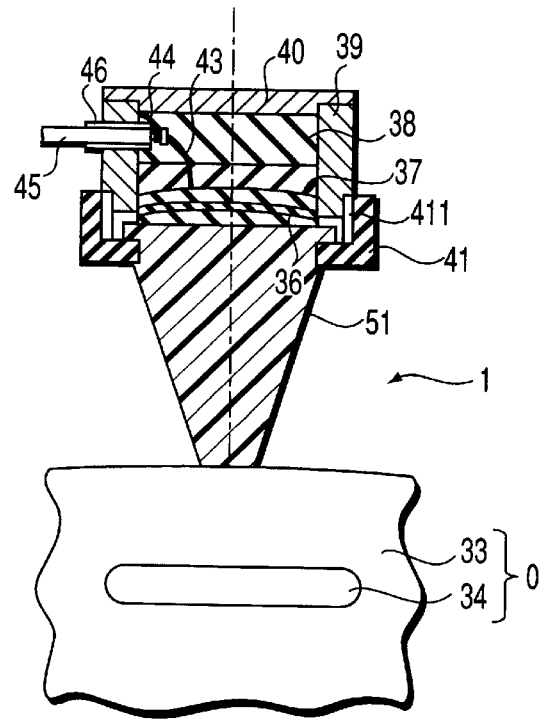
FIG. 8 is a view showing the arrangement of an ultrasonic transducer additionally having an acoustic delay medium.

FIG. 8 shows the second modification. In addition to the features shown in FIG. 7, a portion of an acoustic delay medium 51, which does not serve as a propagation path, is cut off in accordance with the convergent sonic field of ultrasonic waves.

With this structure, it is possible to reduce the portion of the ultrasonic transducer 1, which is brought into contact with the target measurement object O, and thereby perform more accurate measurement.

Figure 9:
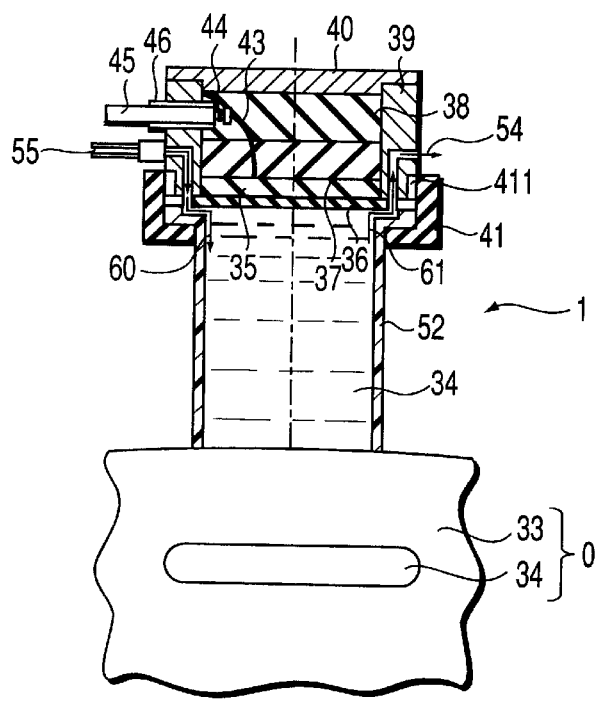
FIG. 9 is a view showing the arrangement of an ultrasonic transducer additionally having an acoustic delay medium.

FIG. 9 shows the third modification which uses a liquid delay medium as an acoustic delay medium, i.e., a liquid acoustic coupling medium.

In FIG. 9, reference numeral 53 denotes a liquid delay medium; 52, a vessel for holding the liquid delay medium 53; 55, an injection port for injecting the liquid delay medium 53; 60, an arrow indicating the way the liquid delay medium 53 is injected; 54, a discharge port for discharging an excess liquid delay medium 53; and 61, an arrow indicating the way the liquid delay medium 53 is discharged.

The rest of the structure is exactly the same as in FIG. 6.

The piezoelectric element can have a concave surface as shown in FIG. 7, or the holding vessel 52 can be tapered toward the end as shown in FIG. 8.

Additionally, a liquid solution mixture having low viscosity can be used as the liquid delay medium 53 and evenly rotated in the vessel against no viscosity resistance, thereby obtaining high-quality acoustic impedance images.

As this liquid acoustic delay medium, liquid paraffin having an acoustic impedance close to that of a living body and low viscosity is suitable.

When the structure as shown in FIG. 9 is used, the thickness of the liquid acoustic delay medium 53 can be reduced because its sonic velocity is generally low. So, the liquid acoustic delay medium 53 can be held in a form close to surface tension.

Accordingly, when the acoustic impedance of the target measurement object O is measured by using the ultrasonic transducer 1, variations in the acoustic impedance caused by the influence of contact pressure can be avoided.

Figure 10:
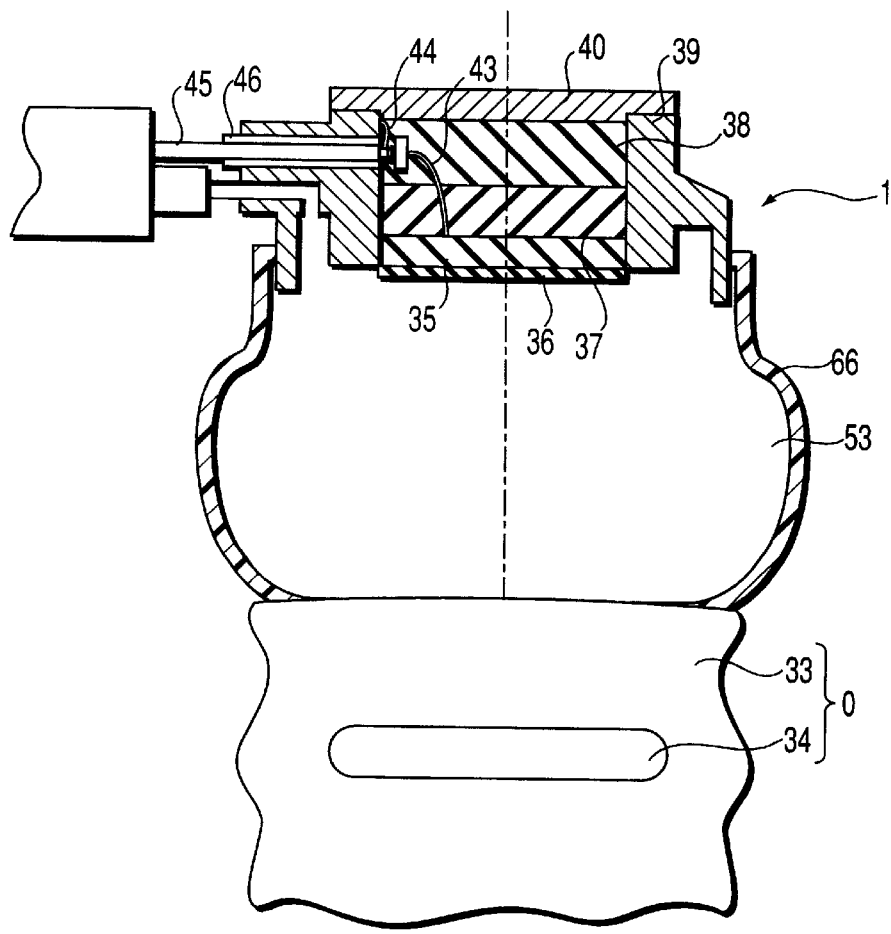
FIG. 10 is a view showing the arrangement of an ultrasonic transducer additionally having an acoustic delay medium.

FIG. 10 shows the fourth modification in which a vessel 66 for holding the liquid acoustic delay medium 53 is made of a latex which is flexible and absorbs ultrasonic waves little.

The liquid acoustic delay medium 53 can be closely confined by thus holding it in a deformable elastic member. This allows stable measurements with no leakage of the liquid acoustic delay medium 53.

Since, however, the distance between the ultrasonic transducer 1 and the target measurement object O varies in accordance with the situation, it is necessary to correct changes in the amplitude of the output signal resulting from this distance variation.

Figure 11:
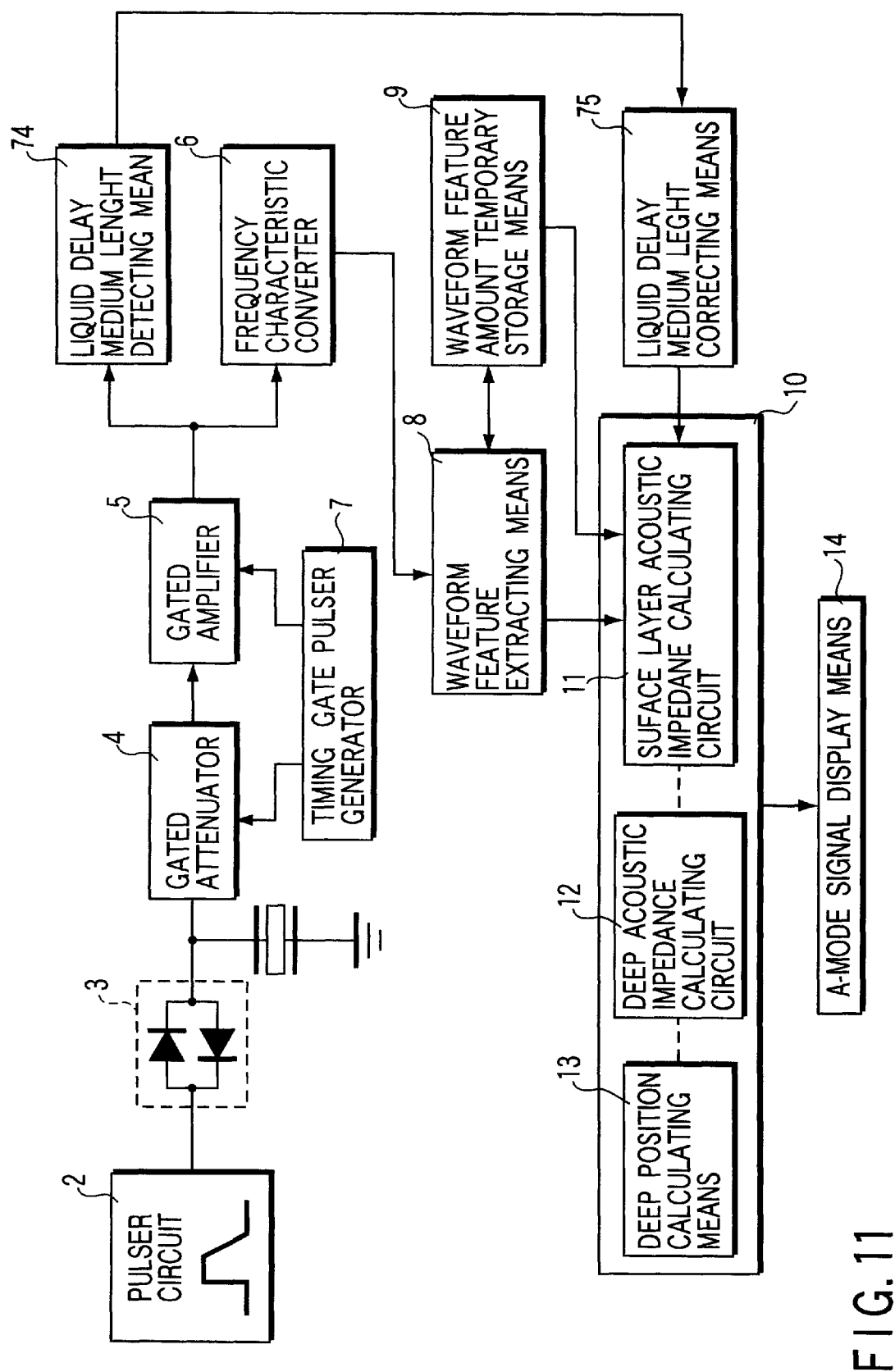
FIG. 11 is a block diagram showing the arrangement of the first embodiment of the present invention further comprising a means for correcting the length of a liquid acoustic delay medium.

FIG. 11 is a block diagram showing an acoustic impedance measuring apparatus as the fifth modification in which a means for correcting changes in the amplitude of an output signal, which are caused by distance variations in the fourth modification, is added to the arrangement shown in FIG. 1.

That is, unlike in the arrangement shown in FIG. 1, a liquid acoustic delay medium length detecting means 74 and a liquid acoustic delay medium length correcting means 75 are connected in series to the output of the gated amplifier 5.

An output from this liquid acoustic delay medium length correcting means 75 is connected to the acoustic impedance calculating means 10.

The liquid acoustic delay medium length detecting means is a circuit for measuring the time the immediate ultrasonic response signal requires to reach the ultrasonic transducer 1 and outputting a distance signal proportional to this time.

Since the sonic velocity of the liquid acoustic delay medium 53 is constant, this distance signal is proportional to the length in the ultrasonic transmission direction of the liquid acoustic delay medium 53.

To correct output signal amplitude changes resulting from distance variations, the liquid acoustic delay medium length correcting means 75 divides the maximum amplitude of the response signal by the reciprocal of the square of the distance signal on the basis of the output signal from the (ultrasonic) liquid acoustic delay medium length detecting means 74.

The method of correcting amplitude changes, however, is not limited to this method.

For example, it is possible to previously measure the sonic field characteristic in the ultrasonic exit direction and avoid the influence of characteristic variations caused by distance variations by using the measured characteristic as a correction distance function.

By correcting amplitude changes in the output signal from the ultrasonic transducer 1 as described above, reliable acoustic impedance data can be obtained.

An acoustic impedance calculation method as one characteristic feature of the present invention will be described below.

In acoustic impedance calculations of the present invention, waveform feature parameters representing the features of a waveform are extracted from the frequency characteristics of the response signal. Of these waveform feature parameters, the acoustic impedance is measured by using parameters having correlations with the acoustic impedance of a target measurement object.

Referring to FIG. 1, the aforementioned trapezoidal or rectangular pulse output from the pulser circuit 2 is applied to the ultrasonic transducer 1 including the acoustic delay medium 42 and the like via the diode circuit 3.

This pulse driving allows the ultrasonic transducer 1 to generate a piezoelectric vibration having a large amplitude and a small signal width by dynamic damping (DD). This piezoelectric vibration propagates as a longitudinal wave in the acoustic delay medium 42 or the like and reaches the interface between the acoustic delay medium 42 or the like and the target measurement object O (FIGS. 6 to 10).

A portion of the piezoelectric vibration enters the target measurement object O, is reflected by the interface, and returns to the ultrasonic transducer 1.

This return time $\tau$ is $\tau=2$ L/Vpp where Vpp and L are, respectively, the sonic velocity and the thickness of the acoustic delay medium 42 or the like.

By the existence of this time $\tau$, the pulse signal and the response signal are observed as separate signals.

The signal that returns after being reflected by the interface, i.e., the surface of the target measurement object O is observed immediately after the pulse signal in the output from the ultrasonic transducer 1. Hence, this signal is called an immediate response signal.

This immediate response signal holds physical property information of the target measurement object O.

The frequency characteristic converter 6 converts the immediate response signal into frequency characteristics. The waveform feature extracting means 8 extracts various waveform feature parameters.

These waveform feature parameters will be described below with reference to FIGS. 12A to 12C.

Figure 12A:
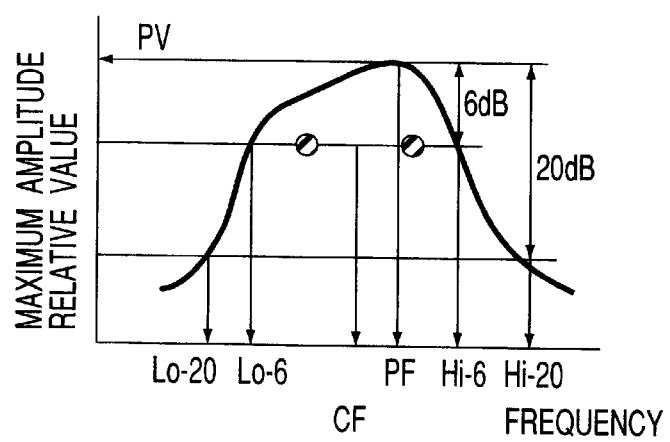

FIGS. 12A to 12C show the frequency characteristics in which the frequency is plotted on the abscissa and a maximum amplitude relative value is plotted on the ordinate.

The maximum amplitude relative value is the relative value of an amplitude at each frequency with reference to a peak voltage (PV).

As shown in FIG. 12A, the frequency which gives the peak voltage (PV) is a peak frequency (PF).

Of frequencies which give amplitude values lower by 6 dB than this peak voltage (PV), the lower frequency is a −6 dB low frequency (Lo−6), and the higher frequency is a −6 dB high frequency (Hi−6).

The frequency intermediate between the −6 dB low frequency (Lo−6) and the −6 dB high frequency (Hi−6) is a center frequency (CF).

The frequency band width between the −6 dB low frequency (Lo−6) and the −6 dB high frequency (Hi−6) is a −6 dB band width (BW−6).

These relationships are represented by

CF=(Lo−6+H1−6)/2

BW−6=Hi−6−Lo−6

As shown in FIG. 12A, of frequencies which give an amplitude value lower by 20 dB than the peak voltage (PV), the lower frequency is a −20 dB low frequency (Lo−20), and the higher frequency is a −20 dB high frequency (Hi−20).

The frequency intermediate between the −20 dB low frequency (Lo−20) and the −20 dB high frequency (Hi−20) is a −20 dB center frequency (CF−20).

The frequency band width between the −20 dB low frequency (Lo−20) and the −20 dB high frequency (Hi−20) is a −20 dB band width (BW−20).

These relationships are represented by

CF−20=(Lo−20+H1−20)/2

BW−20=H1−20=Lo−20

Dividing the −6 dB band width (BW−6) by the center frequency (CF) gives a −6 dB relative band width (rBW−6). Dividing the −20 dB band width by the −20 dB center frequency (CF−20) gives a −20 dB relative band width (rBW−20).

These relationships are represented by rBW-6=BW-6/CF rBW-20=BW-20/CF

Dividing the difference between the peak frequency (PF) and the −6 dB low frequency (Lo-6) by the difference between the −6 dB high frequency (Hi-6) and the peak frequency (PF) gives a −6 dB skew (Skew-6).

Dividing the difference between the peak frequency (PF) and the −20 dB low frequency (Lo-20) by the difference between the −20 dB high frequency and the peak frequency (PF) gives a −20 dB skew (Skew-20).

These relationships are represented by

Skew-6=(CF−Lo-6)/(H1-6−CF)

Skew-20=(CF−Lo-20)/(H1-20−CF)

As shown in FIG. 12B, a frequency interval from a predetermined frequency f1 lower than the center frequency to a predetermined frequency f6 higher than the center frequency is equally divided into five intervals (f1, f2, f3, f4, f5, and f6).

The central one of these five equal frequency intervals contains the center frequency.

The product of the band width and the amplitude is calculated for each of these five equal frequency intervals.

These products are band width-amplitude products B1 to B5.

Note that the bands of these band width-amplitude products B1 to B5 can be properly changed.

As shown in FIG. 12C, an amplitude Xi at each frequency i is used to calculate a first moment (1st-Moment) and a second moment (2nd-Moment) by $$1stMoment = \sum_i i \cdot Xi / \sum Xi$$

$$2ndMoment = \sum_i (i - 1stMoment)^2 Xi / \sum xi$$

Also, the polarity (PhasePN) of a phase at the peak frequency is extracted as a parameter.

In FIG. 1, the waveform feature extracting means 8 extracts these waveform feature parameters explained above after the frequency feature converter 6 converts the immediate response signal into frequency characteristics.

It was experimentally confirmed that some of the waveform feature parameters of the immediate response signal described above reflect the complex acoustic impedance and the complex elastic modulus as the physical properties of a target measurement object.

FIGS. 13 to 16 show the experimentally obtained relationships between the peak voltage (PV) and band-amplitude product (B2) selected as examples of the above waveform feature parameters, the complex acoustic impedance, and the complex elastic modulus.

FIG. 13 plots the relationship between the peak voltage (PV) and the complex acoustic impedance.

The abscissa of FIG. 13 indicates ΔPV which is the ratio of PV when a target measurement object exists to PV when no target measurement object exists (no-load).

The ordinate of FIG. 13 indicates a real part Zreal and an imaginary part Zimag of the complex acoustic impedance.

In FIG. 13, black circles indicate measurement values in the real part of the complex acoustic impedance, and white circles indicate measurement values in the imaginary part of the complex acoustic impedance.

Also, in FIG. 13, the solid line is the line of linear regression calculated from the correlation between ΔPV and Zreal, and the broken line is the line of linear regression calculated from the correlation between ΔPV and Zimag.

Mathematical expressions shown in FIG. 13 are linear regression expressions obtained from the experimental results, where R is a correlation coefficient.

Figure 14:
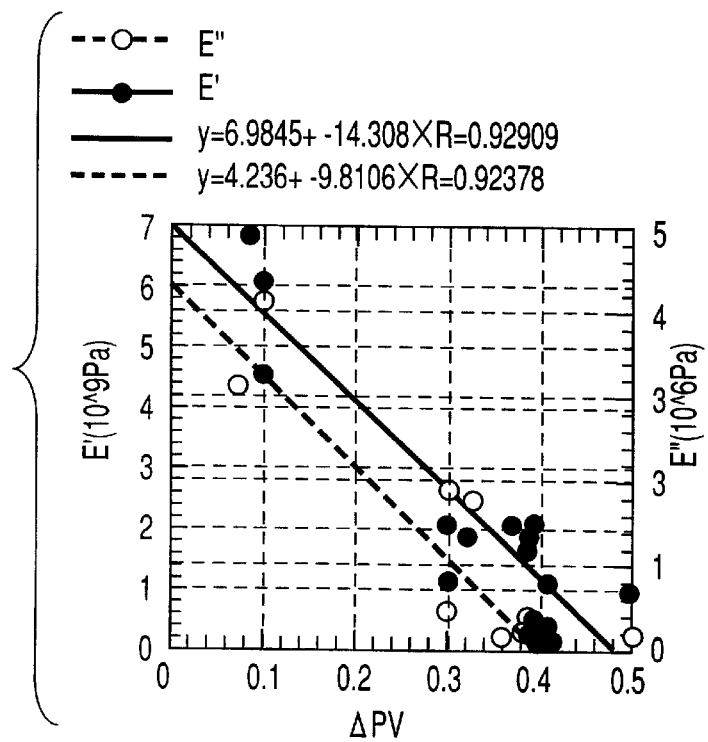
FIG. 14 is a graph showing experimental results for explaining the relationship between the waveform feature parameter (PV) and elasticity modulus.

FIG. 14 plots the relationship between the peak voltage (PV) and complex elastic modulus. Similar to FIG. 13, the abscissa indicates ΔPV, and the ordinate indicates a real part E' and an imaginary part E" of the complex elastic modulus.

Figure 15:
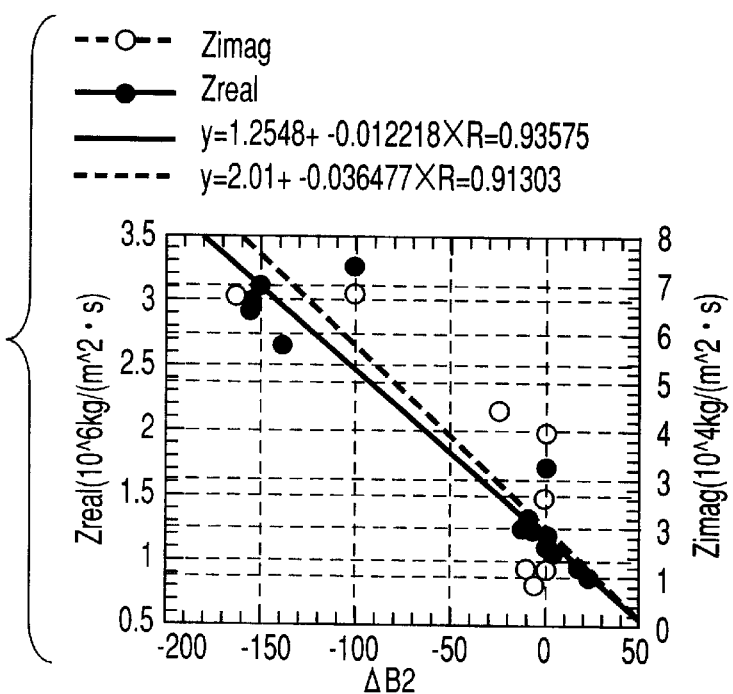
FIG. 15 is a graph showing experimental results for explaining the relationship between a waveform feature parameter (B2) and acoustic impedance.

FIG. 15 plots the relationship between the band-amplitude product (B2) and complex acoustic impedance. The abscissa indicates ΔB2 which is the difference between B2 when a target measurement object exists and B2 when no target measurement object exists (no-load). The ordinate indicates the real part Zreal and the imaginary part zimag of the complex acoustic impedance.

Figures 16, 17:
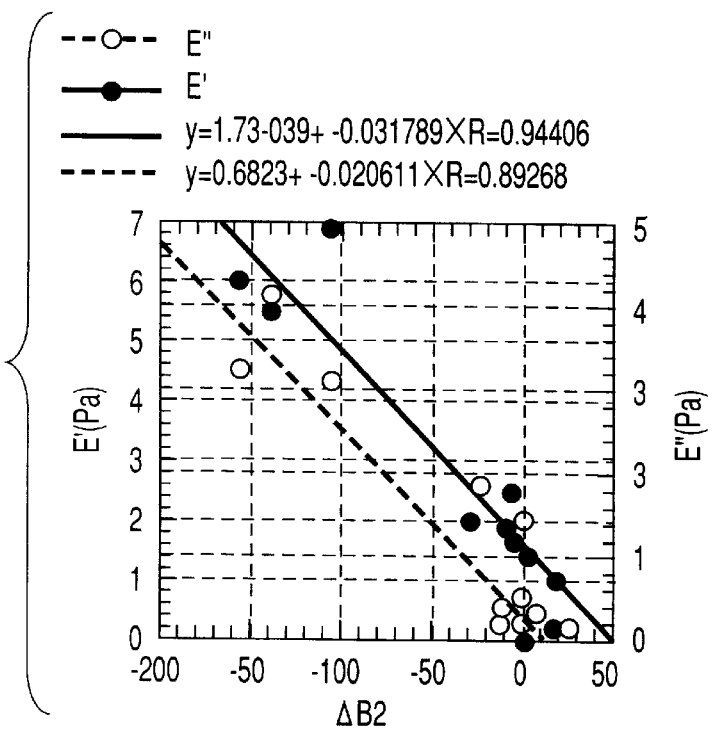
FIG. 16 is a graph showing experimental results for explaining the relationship between the waveform feature parameter (B2) and elasticity modulus.
FIG. 17 is a view showing the correlation between the waveform feature parameters, acoustic impedance, and elasticity modulus in the form of a table.

FIG. 16 plots the relationship between the band-amplitude product (B2) and complex elastic modulus.

As described above, the ratio of or the difference between the values obtained in a measurement state and a no-load state are calculated for each waveform feature parameter.

Since each waveform feature parameter is not directly used and the ratio of or the difference between its values is calculated, the change width increases. This advantageously improves the measurement accuracy.

For waveform feature parameters other than the peak voltage (PV) and the band-amplitude product (B2), it is also possible to plot experimental results and obtain regression expressions or correlations with the acoustic impedance or the elastic modulus in the same manner as in FIGS. 13 to 16.

FIG. 17 shows a list of correlation coefficients representing the correlations between principal waveform feature parameters and the real and imaginary parts of the acoustic impedance and elastic modulus.

As is apparent from FIG. 17, the peak voltage (PV) and the band-amplitude width (B2) taken as examples in the above description have strong correlations having correlation coefficients of 0.9 or more.

Figure 18:
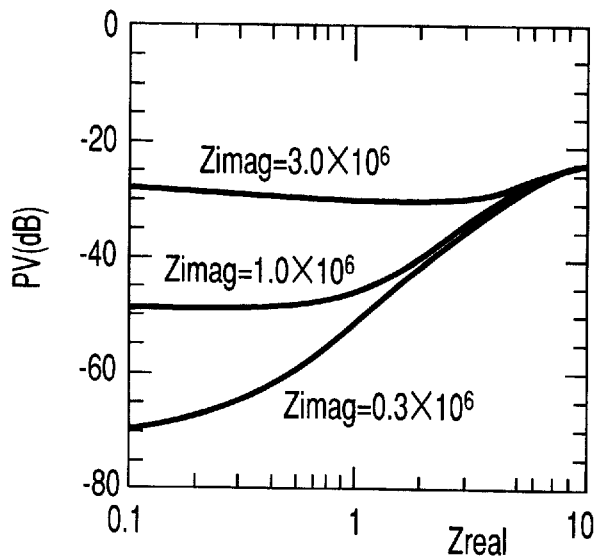
FIG. 18 is a graph showing simulation results for explaining the relationship between the waveform feature parameter (PV) and acoustic impedance.
Figure 19:
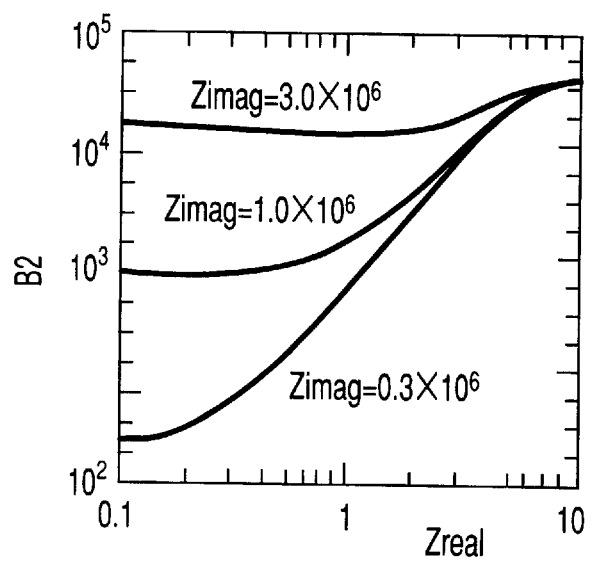
FIG. 19 is a graph showing simulation results for explaining the relationship between the waveform feature parameter (B2) and acoustic impedance.

FIGS. 18 and 19 show the results of simulations performed by using Mason's equivalent circuits to theoretically back up these experimental results.

FIG. 18 shows the relationship between the peak voltage (PV) and the real part Zreal and imaginary part Zimag of the acoustic impedance. That is, FIG. 18 is a graph showing the relationship between Zreal and PV for various Zimag values.

Analogously, FIG. 19 shows the relationship between the band-amplitude product (B2) and the real part Zreal and imaginary part Zimag of the acoustic impedance.

These simulation results also back up the correlations, qualitatively.

The peak voltage (PV) and the band-amplitude product (B2) have been described as waveform feature parameters having strong correlations with the acoustic impedance and the elastic modulus of a target measurement object.

As is apparent from the table in FIG. 17, however, many other waveform feature parameters also have sufficient correlations. In particular, any of the following correlations has a correlation coefficient exceeding 0.5: ΔPF and the real and imaginary parts of the acoustic impedance and the imaginary part of the elastic modulus; ΔCF and the real part of the acoustic impedance and the real part of the elastic modulus; ΔLo-6 and the real part of the acoustic impedance and the real part of the elastic modulus; ΔB1 and the real and imaginary parts of the acoustic impedance and the real and imaginary parts of the elastic modulus; ΔB4 and the real part of the elastic modulus; 1stMoment and the real and imaginary parts of the acoustic impedance and the real and imaginary parts of the elastic modulus; and 2ndMoment and the real and imaginary parts of the acoustic impedance and the real and imaginary parts of the elastic modulus.

When these parameters are used instead of $\Delta PV$ or $\Delta B2$, therefore, they may exhibit larger correlations than $\Delta PV$ or $\Delta B2$ depending on the setting conditions of the measuring apparatus and the characteristics of the ultrasonic transducer 1. Consequently, the physical properties of a target measurement object may be estimated more accurately than when $\Delta PV$ or $\Delta B2$ is used.

In the present invention, the acoustic impedance and the elastic modulus are estimated by the following method by using the correlations between the above-mentioned waveform feature parameters and the acoustic impedance and elastic modulus of a target measurement object.

First, the following calibration expressions are used to calculate the acoustic impedance from the waveform feature parameters $$Zreal = a1 \cdot \Delta P1 + a2 \cdot \Delta P2 + a3$$

$$Zimag = b1 \cdot \Delta P1 + b1 \cdot \Delta P2 + b3$$

where Zreal is the real part of the acoustic impedance, Zimag is the imaginary part of the acoustic impedance, $\Delta P1$ and $\Delta P2$ are extracted waveform parameters, and a1, a2, a3, b1, b2, and b3 are constants.

Also, the following calibration expressions are used to calculate the elastic modulus from the waveform feature parameters $$Ereal = c1 \cdot \Delta P1 + c2 \cdot \Delta P2 + c3$$

$$Eimag = d1 \cdot \Delta P1 + d2 \cdot \Delta P2 + c3$$

where Ereal is the real part of the elastic modulus, Eimag is the imaginary part of the elastic modulus, $\Delta P1$ and $\Delta P2$ are the extracted waveform feature parameters, and c1, c2, c3, d1, d2, and d3 are fixed constants.

In the above calibration expressions, the coefficients of the regression expressions based on the aforementioned experimental data are directly used as the constants a1, a2, b1, b2, c1, c2, d1, and d2.

The fixed constants a3, b3, c3, and d3 are identified by using a living body phantom material having a known thickness and density and characteristics close to the characteristics of a vital tissue. Zreal, Zimag, Ereal, and Eimag of this living body phantom material are strictly evaluated in accordance with the relationship between the thickness, density, and front and back surface reflected echo signals.

$\Delta P1$ and $\Delta P2$ are desirably $\Delta PV$ and $\Delta B2$ as described above.

More specifically, preferable expressions for evaluating the acoustic impedance are $$Zreal = -5.63\Delta PV + 0.0122\Delta B2 + 3.31$$

$$Zimag = -17.8\Delta PV + 0.0365\Delta B2 + 14.7$$

The flow to the above calculations will be described below with reference to FIGS. 1 and 6 to 10.

The signal from the ultrasonic transducer 1 including the acoustic delay medium 42 and the like has the immediate ultrasonic response signal reflected by the interface between the acoustic delay medium 42 or the like and the target measurement object O.

This immediate ultrasonic response signal is attenuated in a certain time region and amplified in another time region by the gated attenuator 4 and gated amplifier 5 controlled by the timing gate pulse generator 7. Consequently, the immediate ultrasonic response signal is separated from the other signal and adjusted to have an optimum amplitude.

The immediate ultrasonic response signal is then AD-converted by the frequency characteristic converter 6 and subjected to FFT processing. This converts the time characteristics of the signal into frequency characteristics.

The frequency characteristics are input to the waveform feature extracting means 8 where waveform feature parameters are calculated in accordance with the above definitions.

In the above calibration expressions, as indicated by $\Delta$ affixed to each symbol, each waveform feature parameter is used in the form of the ratio of or the difference between a value obtained when a target measurement object is measured and a value when no load is applied.

It is, therefore, necessary to previously measure the values of no-load waveform feature parameters and store them in the waveform feature amount temporary storage 9.

In this embodiment, the maximum amplitude of reflected echo with no load is larger than in any case. Therefore, a threshold value which is 80 to 90% of this maximum amplitude is set, and the waveform feature amount temporary storage means 9 detects this threshold value at all times. If the threshold value is exceeded, it is determined that measurement is performed with no load. Hence, the waveform feature amount temporary storage means 9 stores the waveform feature parameter calculated by the waveform feature extracting means 8.

If the threshold value is not exceeded, it is determined that a target measurement object is measured. Therefore, the waveform feature parameter is directly input to the surface layer acoustic impedance calculating circuit 11 which calculates the ratio of or the difference between this waveform feature parameter and the no-load waveform feature parameter stored in the waveform feature amount temporary storage means 9.

This calculation result is further substituted into the above expressions to calculate the acoustic impedance and the elastic value.

If information of the in-plane distribution of the physical properties of the target measurement object O is necessary, the ultrasonic transducer 1 or the target measurement object O is scanned in the direction of plane, and the acoustic impedance is measured by the above method in each position.

In this manner, the present invention can obtain the surface distribution of the acoustic impedance of the target measurement object O, i.e., a C-mode image.

The acoustic impedance calculation method described so far can estimate the acoustic impedance only from the reflected signal from the surface of the target measurement object O, which is obtained by the ultrasonic transducer 1, and does not require any signal reflected by the back surface of the target measurement object O.

In the present invention, therefore, the thickness of the target measurement object O need not be known in advance. Also, if the density of the target measurement object O can be assumed, the thickness of the target measurement object O can be similarly estimated without any signal reflected by the back surface.

The present invention is also advantageous in the ability of real-time processing because mathematical expressions are simple.

Furthermore, the present invention uses a relatively large echo signal in the boundary of acoustic impedances. Therefore, the signal is not buried in noise, so the physical properties of a target measurement object can be evaluated with high reliability.

In contrast, the prior art uses a signal with an extremely low level from a fine scattering body in a vital tissue. Hence, it is highly likely that the signal is buried in external noise or apparatus noise.

In the present invention as described above, the acoustic impedance near the surface of a target measurement object can be measured on the basis of the immediate ultrasonic response signal.

In, e.g., actual medical applications, however, if an abnormal tissue such as a tumor exists in a position in the direction of depth from a normal tissue, it is desirable to detect information concerning the position and the degree of the abnormality as physical property values of the tissue.

This means that a target measurement object including a plurality of layers having different physical property values in the direction of depth is expressed absolutely or relatively by the physical property values, such as the acoustic impedance and the elastic modulus, in units of layers.

Measurement of the acoustic impedance in a deep portion of a target measurement object will be described below.

Referring to FIG. 1, the deep acoustic impedance calculating circuit 12 and the deep position calculating means 13 are functional blocks pertaining to this measurement.

Calculations of the deep acoustic impedance calculating circuit 12 and deep position calculating means 13 will be described below.

Assume that a target measurement object has a three-layered structure, and let Zn be the acoustic impedance of the nth layer of the target measurement object and Zrealn and Zimagn be the real and imaginary parts, respectively, of this Zn.

(1) First, an acoustic impedance Z1 (Z1=Zreal1+jZimag1) of the first layer is measured by the aforementioned method using the immediate ultrasonic response signal.

(2) The thickness of the first layer, i.e., the position of the boundary between the first and second layers is estimated.

This boundary position is estimated from the time difference between ultrasonic echo signals reflected by the boundary surface between the first and second layers, the density assumed to be 1,000 kg/m$^3$ (close to the density of a human body tissue), and Zreal calculated above.

(3) The following quadratic equations in which an acoustic impedance Z2 (Z2=Zreal2+jZimag2) of the second layer is an unknown variable are solved for the real and imaginary parts $$Re\{Z2^2+2\cdot Z1\cdot Z2+Z1^2\cdot(K1+1)-K1\cdot Zprop\}=0$$

$$Im\{Z2^2+2\cdot Z1\cdot Z2+Z1^2\cdot(K1+1)-K1\cdot Zprop\}=0$$

where K1=B1·B2/A0·B3,
A0: the maximum amplitude of an echo reflected by the interface between the acoustic delay medium and the target measurement object
B1: the maximum amplitude of an echo reflected by the interface between the first and second layers of the target measurement object
B2: the maximum amplitude of an echo reflected by the interface between the second and third layers of the target measurement object
B3: the maximum amplitude of an echo reflected by the back surface (air load) of the third layer
Zprop: the acoustic impedance of the acoustic delay medium
Re{ }: calculation of the real part
Im{ }: calculation of the imaginary part
(4) In accordance with the two solutions of each of the two equations calculated in (3), values larger than Zreal1 are used if the phase at the maximum amplitude of the echo signal is positive, and values smaller than Zreal1 are used if the phase is negative, as Zreal2 and zimag2, respectively.
(5) Assuming that the density of the second layer is 1,000 kg/m$^3$ as in (2), the thickness of the second layer, i.e., the position of the interface between the second and third layers is estimated.
(6) A maximum amplitude Bn of a reflected echo signal from the interface between the (n−1)th and nth layers of a target measurement object constructed of n layers is represented by $$Bn = \left[\prod_{i=1}^{n} \left\{\frac{4^i Z_{i-1} \cdot Z_i}{(Z_{i-1}+Z_i)} \exp(-2\alpha i \cdot di)\right\}\right] \times \frac{Z1+Z0}{Z1-Z0} A0$$

where
A0: the maximum amplitude of an echo reflected by the interface between the acoustic delay medium and the target measurement object
$Z_{i-1}$: the acoustic impedance of the (i−1)th layer
Z1: the acoustic impedance of the first layer estimated from the waveform feature parameters and the calibration expressions
Z0: Zprop
αi: ultrasonic attenuation in the first layer
d: the thickness of the first layer
Zreal3 can be estimated since n=4, i.e., Z4<<Z3 (Z4 is the impedance of an air layer and known) from the expression of B4 and α4 is substantially 0.

Also, assuming that the density is 1,000 kg/m$^3$, a thickness d3 of the third layer is estimated.

α3 is obtained because n=3, i.e., the value of α3·d3 can be calculated from the expression of B3.

Since the attenuation α and Eimag have a relationship Eimag=ραV$^3$/πfc, Eimag can be calculated by assuming the density is 1,000 kg/m$^3$, and Zimag can be estimated from the relationship between Eimag and Zimag indicated by Zimag=(Ereal$^2$+Eimag$^2$)¼·sin{Arctan(Eimag/Ereal)/2}

Ereal=ρV$^2$

The deep acoustic impedance calculating circuit 12 and the deep position calculating means 13 rapidly perform these calculations. This allows the A-mode signal display means 14 to display the relationship between the position and acoustic impedance along the axis of an ultrasonic beam.

The above method uses echo signals from boundary layers having different acoustic impedances. Therefore, the signal amplitude is relatively large, and this makes easy reduction of noise and high-accuracy measurement feasible.

Also, the waveform feature parameters extracted from the frequency characteristics can be calculated within a very short time. Hence, the real-time processability is not degraded by complicated calculations, unlike in the prior art.

Furthermore, since no vibrating mechanism is necessary, the apparatus can be miniaturized and applied to the conventional ultrasonic endoscopes.

Second Embodiment

As described in the above first embodiment, by adding the acoustic delay medium 42 and the like to the ultrasonic transducer 1, the pulse signal and the immediate ultrasonic response signal can be separated with no difficulties in circuit design.

Multiple reflection, however, generated in the acoustic delay medium 42 or the like sometimes interferes with an echo signal from a deep portion in the target measurement object O.

This may distort target measurement object physical property information contained in the echo signal and lower the reliability of detection by the ultrasonic transducer 1, depending on the relationship between the length of the acoustic delay medium 42 or the like and the diagnostic distance to the target measurement object O.

In this second embodiment, therefore, an acoustic impedance measuring apparatus in which the acoustic delay medium 42 and the like need not be added to the ultrasonic transducer 1 will be described.

Referring to FIG. 20, a pulser circuit 2 outputs a trapezoidal or rectangular pulse signal, and a branching circuit 15 branches this pulse signal into two equivalent signals.

As in the first embodiment, one of the branched signals is input to an ultrasonic transducer 19 via a diode circuit 3.

Since no acoustic delay medium is added to this ultrasonic transducer 19, the ultrasonic transducer 19 superposes the drive pulse signal and the immediate ultrasonic response signal and transmits the superposed signal to a gated attenuator 4 and a gated amplifier 5.

The voltage of the drive pulse signal is normally 100V or more. Therefore, the gated attenuator 4 attenuates the voltage to substantially 1V only during the period in which the drive pulse signal continues. After that, the gated amplifier 5 amplifies the voltage.

After this amplification, the signal is input to one input terminal of a subtracting circuit 20.

Meanwhile, the other signal branched by the branching circuit 15 is input to the other input terminal via an attenuator 16 and a delay circuit 17.

The attenuator 16 attenuates the signal to an appropriate voltage applicable to the subtracting circuit 20. This attenuator 16 has a function of adjusting the attenuation in accordance with the voltage of the driving waveform.

The delay circuit 17 gives a delay equivalent to a phase delay produced when the signal passes through the diode circuit 3, the ultrasonic transducer 19, the gated attenuator 4, and the gated amplifier 5 arranged on the other branched path. The delay circuit 17 can adjust its delay time.

This delay time is so set that the amplitude of a surge voltage is a minimum at the leading or trailing edge when the drive pulse signal is a trapezoidal signal, or at the two rise times when the drive pulse signal is a rectangular signal.

When this adjustment is performed, the output from the subtracting circuit 20 becomes an ultrasonic pulse string having no traces of the driving pulse signal and having only the immediate ultrasonic response signal and the succeeding ultrasonic echo signal.

A processing method after the output from the subtracting circuit 20 has the same means, functions, and effects as the contents described in the first embodiment, so a detailed description thereof will be omitted.

However, the adjustment of the attenuation degree of the attenuator 16 and the adjustment of the delay time of the delay circuit 17 are not restricted to the above methods.

For example, the adjustment can also be performed such that the output from the subtracting circuit 20 is a minimum with the ultrasonic transducer 19 in a no-load state.

In this second embodiment, no acoustic delay medium needs to be added to the ultrasonic transducer, so no multiple signal is produced because there is no acoustic delay medium. This eliminates the interference between the multiple signal and the ultrasonic echo signal and allows reliable ultrasonic echo signal detection.

Also, the second embodiment uses the difference between two signals. Accordingly, it is possible to suppress variations in the trapezoidal waveform as a pulse signal resulting from variations in the power-supply voltage, or variations in the waveform feature parameters caused by variations in the base line. This makes more accurate measurements possible.

Third Embodiment

The third embodiment of the present invention will be described below with reference to FIG. 21.

In the above first and second embodiments, the measurement results are displayed in the form of an A-mode signal, i.e., the values of the acoustic impedance and the elastic modulus as elastic characteristics in positions in the direction of depth on the axis of one ultrasonic beam are plotted.

In this third embodiment, an ultrasonic beam is mechanically or electronically scanned to display the values of the acoustic impedance and the elastic modulus in B mode, i.e., in the form of a tomographic image.

In addition, this third embodiment has a function of displaying an image by superposing it on an ultrasonic B-mode image reconstructed by the conventional method.

Figure 21:
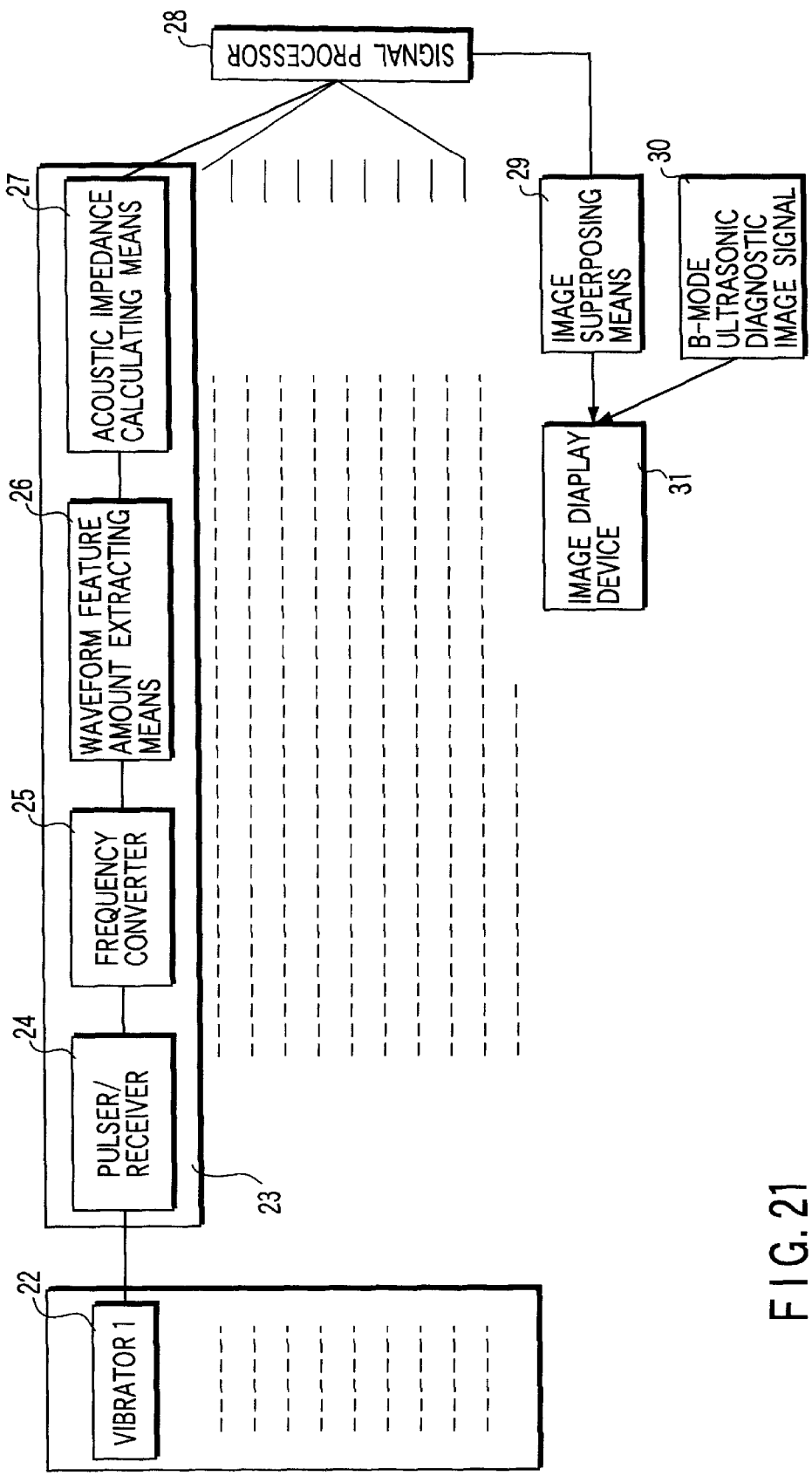
FIG. 21 is a block diagram showing the arrangement of main part of the third embodiment of the present invention.
Figure 22A:
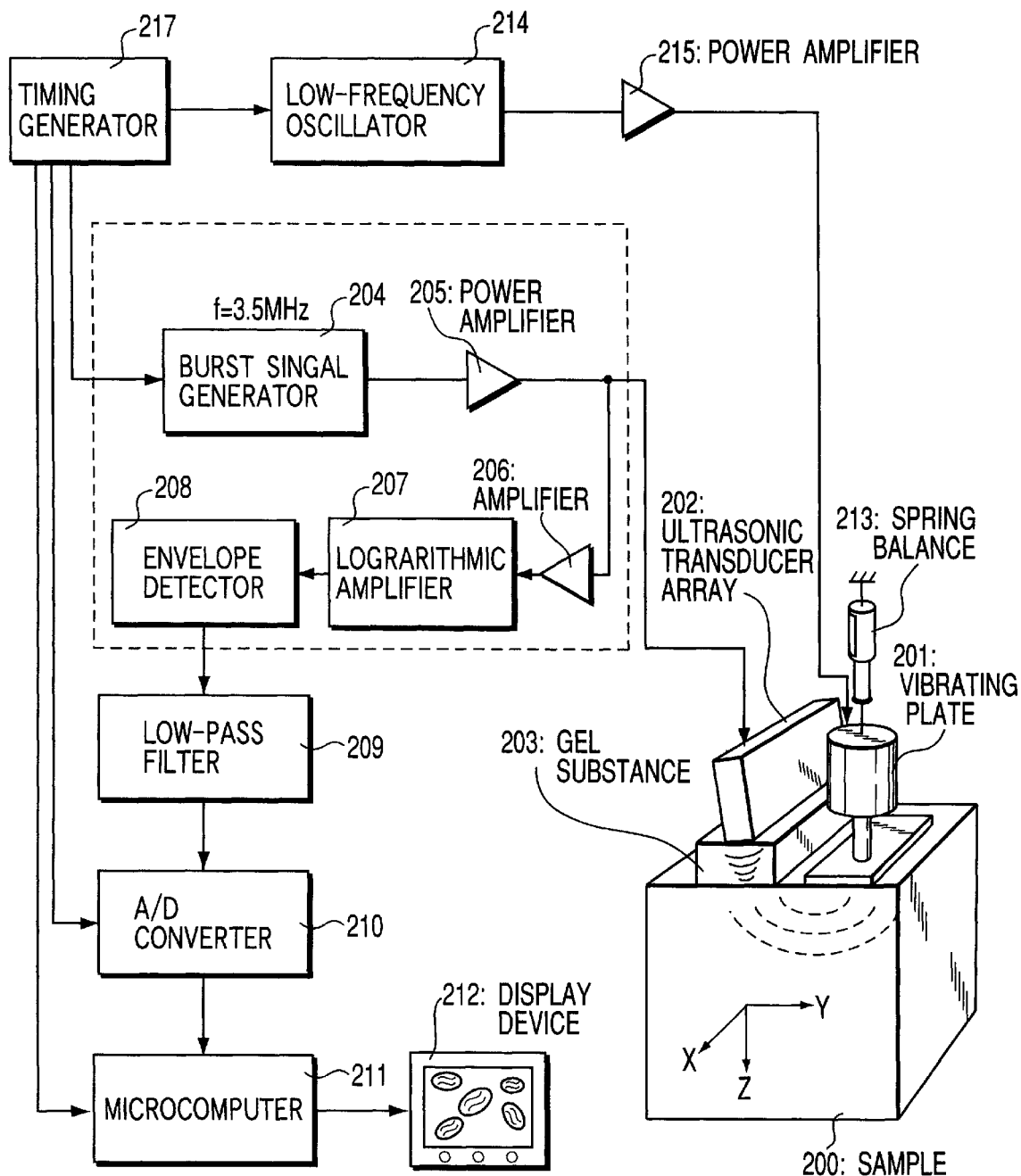
FIGS. 22A to 22D are views for explaining the arrangement and waveforms of the first prior art.
Figure 22B:
Figure 22C:
Figure 22D:
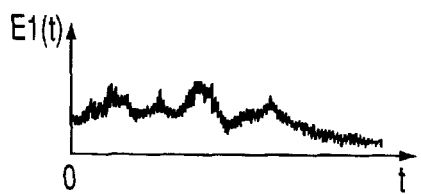
Figure 23A:
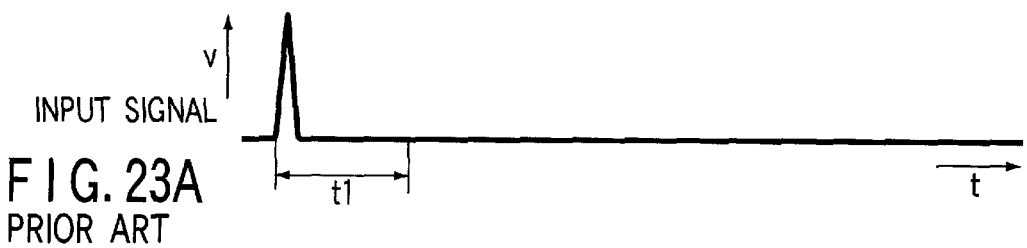
FIGS. 23A to 23D are views for explaining the waveforms of the second prior art.
Figure 23B:
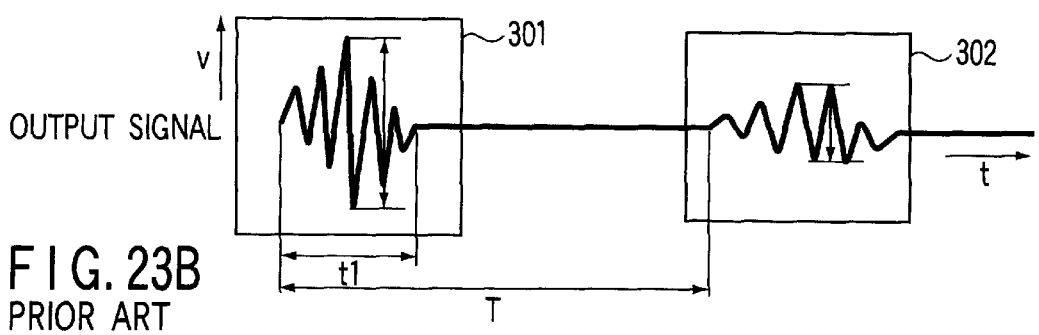
Figure 23C:
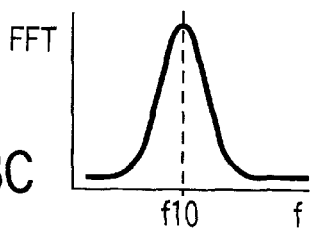
Figure 23D:
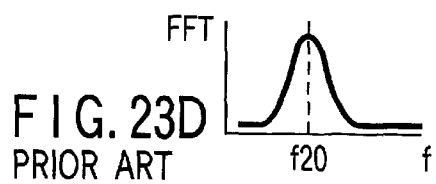
Figure 24:
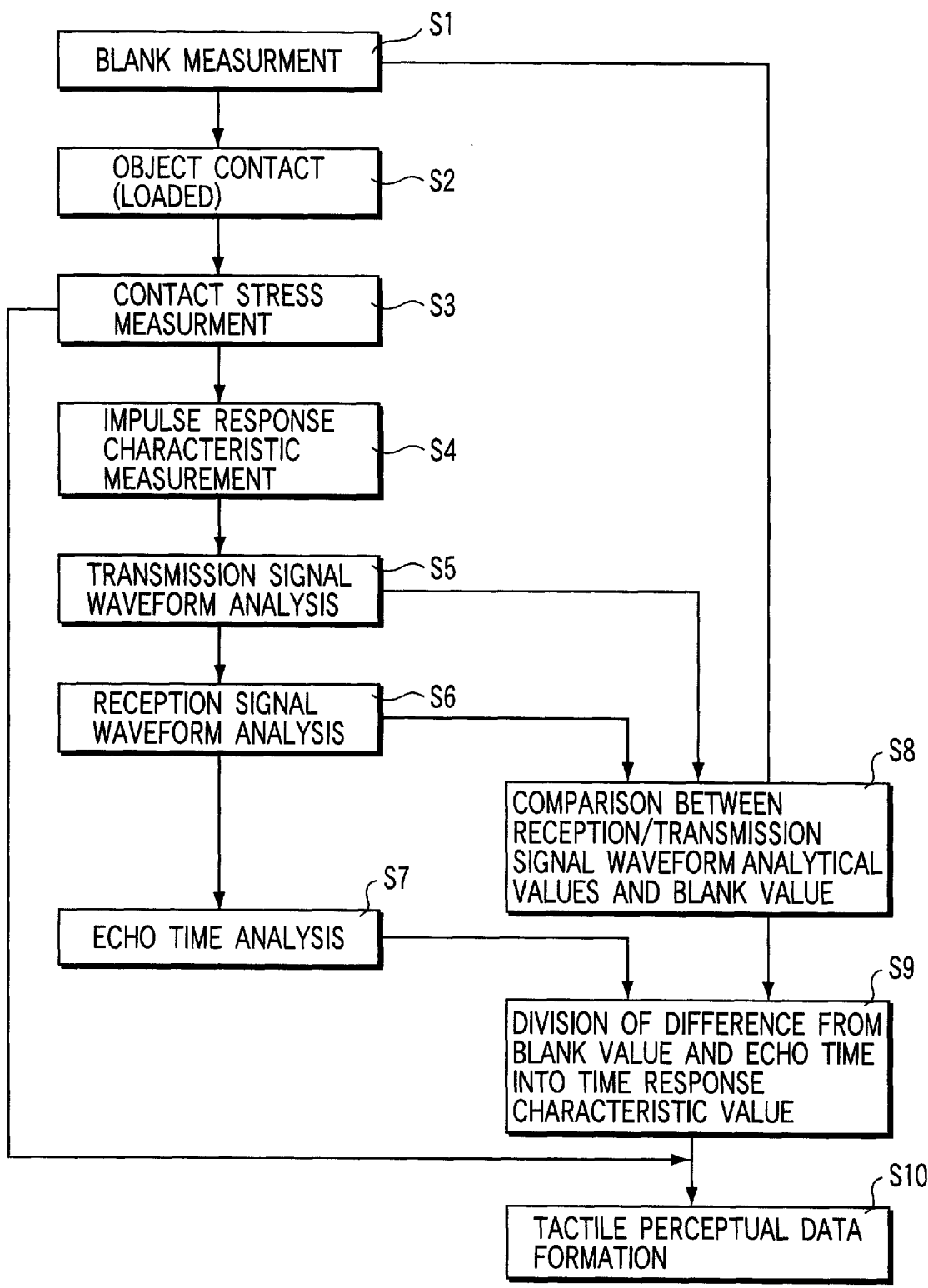
FIG. 24 is a flow chart for explaining the process flow of the second prior art.

In an ultrasonic transducer 21 shown in FIG. 21, N piezoelectric vibrators 22 are arrayed in a line, or N×M piezoelectric vibrators 22 are two-dimensionally arrayed.

Outputs from these arrayed piezoelectric vibrators 22 are input to signal processing channels 23 equal in number to the piezoelectric vibrators 22.

Each signal processing line 23 includes a pulser/receiver 24 corresponding to the gated attenuator 4 and the gated amplifier 5 in the first and second embodiments, a frequency characteristic converter 25, a waveform feature extracting means 26, an acoustic impedance calculating means 27, and the like.

In short, each signal processing channel 23 is constructed of electronic circuits similar to those in the first and second embodiments.

Since, however, the structure of the ultrasonic transducer 21 is different from that of the ultrasonic transducer 1 in the first and second embodiments, it is necessary to use waveform feature parameters and calibration expressions having different contents.

A signal processor 28 collects the outputs from the signal processing channels 23 and forms a B-mode image.

This image is input to an image superposing means 29 and can be displayed, together with an output from a conventional B-mode ultrasonic diagnostic image signal unit 30, on the same screen of an image display device 31.

As described above, this third embodiment provides an acoustic impedance evaluation system including a plurality of acoustic impedance evaluation channels and a signal processing means for obtaining a B-mode image from a plurality of acoustic impedances obtained by these channels.

In the third embodiment with this arrangement, important medical diagnostic information which cannot be obtained by the conventional ultrasonic diagnoses can be obtained.

In this third embodiment, the state of the acoustic impedance of a target measurement object can be two-dimensionally monitored and superposed on a conventional ultrasonic tomographic image. So, details of the state of the target measurement object can be known.

Appendix

Examples of arrangements representing the characteristic features of the present invention which can be extracted from the description of the above embodiments will be added below.

1. An acoustic impedance measuring apparatus is characterized by comprising:
   an ultrasonic transducer;
   a pulse signal generating means for generating a pulse signal to be applied to the ultrasonic transducer;
   a signal separating means for separating, from an output from the ultrasonic transducer, an immediate ultrasonic response signal generated by the ultrasonic transducer and superposed on the pulse signal;
   a signal receiving means for receiving, from the output signal from the ultrasonic transducer, an ultrasonic echo signal generated following the immediate ultrasonic response signal by the ultrasonic transducer, and attenuating or amplifying the ultrasonic echo signal;
   a frequency converting means for obtaining frequency characteristics of the immediate ultrasonic response signal;
   a parameter extracting means for extracting predetermined parameters from the frequency characteristics; and
   an acoustic impedance calculating means for calculating an acoustic impedance of the target measurement object by using relations the acoustic impedance and between a frequency characteristic parameter of the parameters extracted by the parameter extracting means, and calculating an acoustic impedance in a deep portion of the target measurement object on the basis of the calculated acoustic impedance of the target measurement object and the ultrasonic echo signal.

According to appendix 1 above, it is possible to obtain an acoustic impedance measuring apparatus which can accurately estimate the elasticity of a target measurement object and can be miniaturized without degrading the real-time processability.

2. An acoustic impedance measuring apparatus described in appendix 1 above is characterized by comprising a plurality of acoustic impedance measuring apparatuses,
   wherein a B-mode image of acoustic impedance is obtained from results of acoustic impedance measurements by the plurality of acoustic impedance measuring apparatuses.

According to appendix 2 above, it is possible to obtain an acoustic impedance measuring apparatus which can obtain important medical diagnostic information not obtainable by the conventional ultrasonic diagnoses, and by which details of the state of a target measurement object can be known.

3. An acoustic impedance measuring apparatus described in appendix 1 above is characterized in that the ultrasonic transducer comprises
   a piezoelectric element having a mechanical quality coefficient of 50 or less,
   a layered load member formed on a surface opposite to an ultrasonic exit surface of the piezoelectric element and having an acoustic impedance of $1 \times 10^5$ to $15 \times 10^6$ $kgm^{-2} sec^{-1}$, and
   an acoustic coupling layer formed on the ultrasonic exit surface.

According to appendix 3 above, it is possible to obtain an acoustic impedance measuring apparatus capable of obtaining a large vibration amplitude because the pulse voltage loss is small, and detecting depth information of an object at high sensitivity.

4. An acoustic impedance measuring apparatus described in appendix 3 above is characterized in that wherein the load member is one of an air layer, cork, and silicone gel having a specific gravity of 0.7 or less.

According to appendix 4 above, it is possible to obtain an acoustic impedance measuring apparatus capable of detecting depth information of an object with high sensitivity because piezoelectric vibrations excited by the piezoelectric element propagate to the load member with little loss.

5. An acoustic impedance measuring apparatus described in appendix 1 above is characterized by further comprising an acoustic delay medium arranged on the ultrasonic exit surface of the ultrasonic transducer.

According to appendix 5 above, it is possible to obtain a reliable acoustic impedance measuring apparatus capable of stably separating the drive pulse signal the ultrasonic transducer and the reflected signal.

6. An acoustic impedance measuring apparatus described in appendix 5 above is characterized in that the acoustic delay medium is a liquid acoustic coupler disposed on a surface of the acoustic coupling layer, which faces the target measurement object.

According to appendix 6 above, it is possible to obtain a reliable acoustic impedance measuring apparatus which does not vary measurement values due to the influence of contact pressure during measurements and which can stably separate the drive pulse signal of the ultrasonic transducer and the reflected signal.

7. An acoustic impedance measuring apparatus described in appendix 6 above is characterized in that the liquid acoustic coupler is liquid paraffin.

According to appendix 7 above, it is possible to obtain an acoustic impedance measuring apparatus capable of outputting high-quality acoustic impedance images because the liquid paraffin has an acoustic impedance close to that of a living body and can be readily made even due to low viscosity.

8. An acoustic impedance measuring apparatus described in appendix 6 above is characterized by further comprising a holding member made of a deformable elastic member to hold the liquid acoustic coupler, and a correcting means for correcting a value of measured acoustic impedance on the basis of a distance between the ultrasonic transducer and the target measurement object.

According to appendix 8 above, it is possible to obtain an accurate and reliable acoustic impedance measuring apparatus because the measurement accuracy improves by the correction.

9. An acoustic impedance measuring apparatus described in appendix 1 or 6 above is characterized in that
   the pulse signal generated by the pulse signal generating means is a trapezoidal wave,
   a rise time of the pulse signal is fixed to not more than ½ of a reciprocal of a center frequency of the ultrasonic transducer, and
   the apparatus further comprises waveform adjusting means capable of independently adjusting a pulse width, fall time, and peak voltage of the pulse signal.

10. An acoustic impedance measuring apparatus described in appendix 1 or 6 above is characterized in that
    the pulse signal generated by the pulse signal generating means is a trapezoidal wave,
    a pulse width of the pulse signal is $(n+¼) \times 1/f0$ where $f0$ is a center frequency of the ultrasonic transducer and n is an integer from 1 to 5, and
    a fall time of the pulse signal is $(r+¼) \times 1/f0$ where r is a real number from 0.5 to 10.

According to appendixes 9 and 10 above, it is possible to obtain an ultrasonic pulse with a small pulse width and thereby obtain an acoustic impedance measuring apparatus having high resolution in the direction of depth and high sensitivity.

11. An acoustic impedance measuring apparatus described in appendix 1 above is characterized in that the pulse signal generated by the pulse signal generating means has a first rectangular wave and a succeeding second rectangular wave.

12. An acoustic impedance measuring apparatus described in appendix 11 above is characterized in that a pulse width of the first and second pulse signals is fixed to ½ of a reciprocal of a center frequency of the ultrasonic transducer, the second pulse signal has the same polarity as the first pulse signal, and the apparatus further comprises a waveform adjusting means capable of independently adjusting a position of the first pulse signal on a time axis, a position of the second pulse signal on the time axis, a peak voltage of the first pulse signal, and a peak voltage of the second pulse signal.

13. An acoustic impedance measuring apparatus described in appendix 12 above is characterized in that a difference between a rise time of the first pulse signal and a rise time of the second pulse signal is an odd-number multiple of ½ of the reciprocal of the center frequency of the ultrasonic transducer.

14. An acoustic impedance measuring apparatus described in appendix 11 above is characterized in that a pulse width of the first and second pulse signals is fixed to ½ of 1/f0 where f0 is a center frequency of the ultrasonic transducer, the second pulse signal is different in polarity from the first pulse signal, and the apparatus further comprises a waveform adjusting means capable of independently adjusting a position of the first pulse signal on a time axis, a position of the second pulse signal on the time axis, a peak voltage of the first pulse signal, and a peak voltage of the second pulse signal.

15. An acoustic impedance measuring apparatus described in appendix 14 above is characterized in that a difference between a rise time of the first pulse signal and a rise time of the second pulse signal is an integral multiple of a reciprocal of the center frequency of the ultrasonic transducer.

According to appendixes 11 to 15 above, it is possible to obtain an ultrasonic pulse with a small pulse width by a simple circuit and thereby obtain an acoustic impedance measuring apparatus having high resolution in the direction of depth and high detection sensitivity.

16. An acoustic impedance measuring apparatus described in appendix 1 above is characterized in that the signal separating means comprises a reference signal forming means for shifting a phase of a signal to adjust an amplitude of the signal, a branching means for branching the signal from the pulse signal generating means into two signals, a connecting means for connecting one output from the branching means to the ultrasonic transducer and the other output to the reference signal forming means, an amplitude adjusting means for attenuating or amplifying the response signal from the ultrasonic transducer in units of time regions, and a subtracting means for subtracting an output signal from the amplitude adjusting means from an output signal from the reference signal forming means.

17. An acoustic impedance measuring apparatus described in appendix 16 above is characterized in that the reference signal forming means comprises an attenuator, amplifier, and delay circuit.

According to appendixes 16 and 17 above, it is possible to obtain a reliable acoustic impedance measuring apparatus because interference by the acoustic delay medium has no influence and the influence of variations in the power supply or base voltage is little.

18. An acoustic impedance measuring apparatus described in appendix 1 above is characterized in that the parameters extracted by the parameter extracting means are any two of a signal peak voltage, center frequency, −3 dB low frequency, −6 dB low frequency, −20 dB low frequency, −3 dB high frequency, −6 dB high frequency, −20 dB high frequency, −3 dB band width, −6 dB band width, −20 dB band width, −3 dB relative band width, −6 dB relative band width, −20 dB relative band width, skew −6 dB, skew −20 dB, band-amplitude product in each band, first moment, and second moment, and polarity of a phase at a peak frequency.

19. An acoustic impedance measuring apparatus described in appendix 18 above is characterized in that one of the two extracted parameters is a peak voltage, and the other parameter is another parameter.

20. An acoustic impedance measuring apparatus described in appendix 19 above is characterized in that one of the two extracted parameters is a peak voltage, and the other parameter is a band-amplitude product in a second-lowest frequency band.

21. An acoustic impedance measuring apparatus described in appendix 1 above is characterized in that the relations are following expressions $$Zreal = a1 \cdot P1 + a2 \cdot P2 + a3$$

$$Zimag = b1 \cdot P1 + b2 \cdot P2 + b3$$

where Zreal is a real part of a complex acoustic impedance, Zimag is an imaginary part of the complex acoustic impedance, P1 is one of the parameters extracted by the parameter extracting means when the target measurement object is measured, P2 is the other parameter extracted by the parameter extracting means when the target measurement object is measured, and a1, a2, a3, b1, b2, and b3 are constants.

22. An acoustic impedance measuring apparatus described in appendix 1 above is characterized in that the relations have a variable which is a difference between or a ratio of a frequency characteristic extracted parameter of an ultrasonic response signal reflected by an end face of the acoustic delay medium in an unloaded state in which the piezoelectric element is not in contact with the target measurement object and a frequency characteristic extracted parameter of an ultrasonic response signal reflected by the end face of the acoustic delay medium in a loaded state in which the piezoelectric element is in contact with the target measurement object.

23. An acoustic impedance measuring apparatus described in appendix 21 above is characterized in that the constants a1, a2, b1, and b2 are values determined by using a plurality of silicone-based resins, a plurality of polyethylene-based resins, and a plurality of living body phantom materials formed at different composition ratios.

According to the inventions in appendixes 18 to 23 above, it is possible to obtain an acoustic impedance measuring apparatus capable of measuring an acoustic impedance without knowing the thickness of the target measurement object and having high real-time processability and high reliability.

24. An acoustic impedance measuring apparatus described in appendix 1 above characterized in that when the target measurement object is constructed of a plurality of layers, an acoustic impedance of each layer below a first layer is calculated by $$Bn = \left[ \prod_{i=1}^{n} \left\{ \frac{4^i Z_{i-1} \cdot Z_i}{(Z_{i-1} + Z_i)} \exp(-2\alpha i \cdot di) \right\} \right] \times \frac{Z1 + Z0}{Z1 - Z0} A0$$

where Bn is a maximum amplitude of an echo signal reflected by a boundary surface between nth and (n−1)th layers, A0 is a maximum amplitude of a surface reflected signal, $Z_{i-1}$ is an acoustic impedance of an (i−1)th layer, Zi is an acoustic impedance of an ith layer, Z1 is an acoustic impedance of the first layer, Z0 is acoustic impedance of a material forming an ultrasonic exit end of the ultrasonic transducer, αi is ultrasonic attenuation in the ith layer, and di is a thickness of the ith layer.

According to the invention described in appendix 24 above, it is possible to obtain an acoustic impedance measuring apparatus capable of high-accuracy measurements, having high real-time processability, and capable of measuring the acoustic impedance in a deep portion of the target measurement object.

According to the present invention, it is possible to obtain an acoustic impedance measuring apparatus capable of measuring the acoustic impedance without knowing the thickness of a target measurement object and having high real-time processability and high reliability.

According to the present invention, it is possible to obtain an acoustic impedance measuring apparatus capable of high-accuracy measurements, having high real-time processability, and capable of measuring the acoustic impedance in a deep portion of a target measurement object.

According to the present invention, it is possible to obtain a reliable acoustic impedance measuring apparatus capable of stably separating the drive pulse signal of the ultrasonic transducer and the reflected signal.

According to the present invention, it is possible to obtain an ultrasonic pulse with a small pulse width and thereby obtain an acoustic impedance measuring apparatus having high resolution in the direction of depth and high detection sensitivity.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An acoustic impedance measuring apparatus for emitting ultrasonic waves to a target measurement object and measuring an acoustic impedance of the target measurement object from ultrasonic waves fed back from the target measurement object, said acoustic impedance measuring apparatus comprising:
   an ultrasonic transducer; and
   a pulser circuit that generates a trapezoidal pulse signal to be applied to said ultrasonic transducer;
   wherein the trapezoidal pulse signal generated by the pulser circuit has a trapezoidal shape having a slope on which a voltage of the pulse signal rises and a slope on which a voltage of the pulse signal falls, and wherein each of the slopes causes vibration of the ultrasonic transducer so as to generate the ultrasonic waves emitted to the target measurement object.

2. An acoustic impedance measuring apparatus according to claim 1, wherein a vibration caused by one slope of the trapezoidal pulse signal and a vibration caused by another slope of the trapezoidal pulse signal cancel each other.

3. An acoustic impedance measuring apparatus according to claim 1, wherein:
   a pulse width of the trapezoidal pulse signal, defined as a time between a rise start time and a fall start time of the trapezoidal pulse signal, is (n+¼)×1/f0 where f0 is a center frequency of the ultrasonic transducer and n is an integer from 1 to 5, and
   a fall time of the trapezoidal pulse signal is (r+¼)×1/f0 where r is a real number from 0.5 to 10.

4. An acoustic impedance measuring apparatus according to claim 1, wherein said apparatus further comprises waveform adjusting means for independently adjusting a pulse width, fall time, and peak voltage of the trapezoidal pulse signal.

5. An acoustic impedance measuring apparatus for emitting ultrasonic waves to a target measurement object and measuring an acoustic impedance of the target measurement object from ultrasonic waves fed back from the target measurement object, said acoustic impedance measuring apparatus comprising:
   an ultrasonic transducer; and
   a pulser circuit that generates a first rectangular pulse signal and a succeeding second rectangular pulse signal, which are to be applied to said ultrasonic transducer;
   wherein the first rectangular pulse signal and the second rectangular pulse signal have different voltages, and the first and second rectangular pulse signals cause vibration of the ultrasonic transducer so as to generate the ultrasonic waves emitted to the target measurement object.

6. An acoustic impedance measuring apparatus according to claim 5, wherein a vibration caused by the second rectangular pulse signal cancels a vibration caused by the first rectangular pulse signal.

7. An acoustic impedance measuring apparatus according to claim 5, wherein said apparatus further comprises waveform adjusting means for independently adjusting a position of the first rectangular pulse signal on a time axis, a position of the second rectangular pulse signal on the time axis, a peak voltage of the first rectangular pulse signal, and a peak voltage of the second rectangular pulse signal.

8. An acoustic impedance measuring apparatus for emitting ultrasonic waves to a target measurement object and measuring an acoustic impedance of the target measurement object from ultrasonic waves fed back from the target measurement object, said acoustic impedance measuring apparatus comprising:
   an ultrasonic transducer; and
   a pulser circuit that generates a signal to be applied to said ultrasonic transducer;
   wherein the signal generated by the pulser circuit causes vibration of the ultrasonic transducer so as to generate the ultrasonic waves emitted to the target measurement object, and wherein a vibration caused by one part of the signal is cancelled by a vibration caused by another part of the signal to suppress the vibration of the ultrasonic transducer from continuing.

* * * * *